US011230525B2

(12) United States Patent
Jeon et al.

(10) Patent No.: US 11,230,525 B2
(45) Date of Patent: Jan. 25, 2022

(54) ORGANIC SULFUR COMPOUND, METHOD FOR PREPARING SAME, AND PHARMACEUTICAL COMPOSITION FOR PREVENTING OR TREATING CANCER OR AN INFLAMMATORY DISEASE, CONTAINING SAME AS ACTIVE INGREDIENT

(71) Applicant: SOOKMYUNG WOMENS UNIVERSITY INDUSTRY-ACADEMIC COOPERATION FOUNDATION, Seoul (KR)

(72) Inventors: Raok Jeon, Seoul (KR); Jae-Ha Ryu, Seoul (KR); Hyewon Cho, Seoul (KR); Yoon-Jung Kim, Incheon (KR); Sang-Hyun Min, Daegu (KR); Ji-Hoon Yu, Seoul (KR)

(73) Assignee: Sookmyung Womens University Industry-Academic Cooperation Foundation, Seoul (KR)

( * ) Notice: Subject to any disclaimer, the term of this patent is extended or adjusted under 35 U.S.C. 154(b) by 565 days.

(21) Appl. No.: 16/317,805

(22) PCT Filed: Jul. 17, 2017

(86) PCT No.: PCT/KR2017/007647
§ 371 (c)(1),
(2) Date: Jun. 4, 2019

(87) PCT Pub. No.: WO2018/012947
PCT Pub. Date: Jan. 18, 2018

(65) Prior Publication Data
US 2021/0300865 A1 Sep. 30, 2021

(30) Foreign Application Priority Data

Jul. 15, 2016 (KR) .......................... 10-2016-0089730
Jul. 15, 2016 (KR) .......................... 10-2016-0089734

(51) Int. Cl.
*C07C 321/20* (2006.01)
*A61P 35/00* (2006.01)

(52) U.S. Cl.
CPC ............ *C07C 321/20* (2013.01); *A61P 35/00* (2018.01)

(58) Field of Classification Search
None
See application file for complete search history.

(56) References Cited

U.S. PATENT DOCUMENTS

2011/0190368 A1* 8/2011 Kaschula ............ A61K 31/4035
514/417

FOREIGN PATENT DOCUMENTS

| EP | 0 185 324 A2 | 6/1986 |
|---|---|---|
| KR | 10-2016-0047657 | 5/2016 |
| WO | WO 2009/065926 A2 | 5/2009 |
| WO | WO 2010/016011 A1 | 2/2010 |

OTHER PUBLICATIONS

Kaschula et al. "Structureeactivity studies on the anti-proliferation activity of ajoene analogues in WHCO1 oesophageal cancer cells," European Journal of Medicinal Chemistry 50 (2012) 236e254 (Year: 2012).*
Michael A. Lea "Organosulfur Compounds and Cancer" *Dietary Phytochemicals in Cancer Prevention and Treatment* 12:147-148 (1996).
Sears et al. "Multiple Ras-dependent phosphorylation pathways regulate Myc protein stability" *Genes & Development* 14:2501-2514 (2000).
Place et al. "HDAC inhibition prevents NF-κB activation by suppressing proteasome activity: Down-regulation of proteasome subunit expression stabilizes IκBα" *Biochemical Pharmacology* 70:394-406 (2005).
Bode et al. "Histone deacetylase inhibitors decrease Toll-like receptor-mediated activation of proinflammatory gene expression by impairing transcription factor recruitment" *Immunology* 122:596-606 (2007).
Hunter et al. "Substituted ajoenes as novel anti-cancer agents" *Bioorganic & Medicinal Chemistry Letters* 18:5277-5279 (2008).
Nian et al. "Allyl mercaptan, a garlic-derived organosulfur compound, inhibits histone deacetylase and enhances Sp3 binding on the P21WAF1 promoter" *Carcinogenesis* 29(9): 1816-1824 (2008).
Reddy et al. "Histone deacetylase inhibition modulates indoleamine 2,3-dioxygenase-dependent DC functions and regulates experimental graft-versus-host disease in mice" *The Journal of Clinical Investigation* 118(7):2562-2573 (2008).
Singh et al. "Nonhistone protein acetylation as cancer therapy targets" *Expert Rev Anticancer Ther.* 10(6):935-954 (2010).
Glauben and Siegmund "Inhibition of Histone Deacetylases in Inflammatory Bowel Disease" *Mol Med* 17(5-6):426-433 (2011).
Kim and Bae "Histone deacetylase inhibitors: molecular mechanisms of action and clinical trials as anti-cancer drugs" *Am J Transl Res* 3(2): 166-179 (2011).
Kaschula et al. "Structure—activity studies on the anti-proliferation activity of ajoene analogues in WHCO1 oesophageal cancer cells" *European Journal of Medicinal Chemistry* 50:236-254 (2012).

(Continued)

*Primary Examiner* — Jeffrey S Lundgren
*Assistant Examiner* — Michael J Schmitt
(74) *Attorney, Agent, or Firm* — Klarquist Sparkman, LLP

(57) ABSTRACT

A novel organic sulfur compound, a method for preparing the same, and a pharmaceutical composition for preventing or treating cancer or inflammatory diseases, containing the same as an active ingredient are provided. The novel organic sulfur compound is capable of excellently inhibiting histone deacetylated (HDAC) enzymes in a concentration of nanomolar or micromolar units and has been found to have an excellent effect against inflammatory diseases, and has been found to be capable of inhibiting the proliferation of cancer.

16 Claims, 5 Drawing Sheets

(56) References Cited

OTHER PUBLICATIONS

Lee et al. "Anti-Inflammatory Activity of Sulfur-Containing Compounds from Garlic" *Journal of Medicinal Food* 15(11)992-999 (2012).
Felice et al. "Selective histone deacetylase isoforms as potential therapeutic targets in inflammatory bowel disease" *Aliment Pharmacol Ther* 41:26-38 (2014).
Kaschula et al. "The Garlic Compound Ajoene Targets Protein Folding in the Endoplasmic Reticulum of Cancer Cells" *Molecular Carcinogenesis* 55(8):1213-1228 (2016).

\* cited by examiner

ORGANIC SULFUR COMPOUND, METHOD FOR PREPARING SAME, AND PHARMACEUTICAL COMPOSITION FOR PREVENTING OR TREATING CANCER OR AN INFLAMMATORY DISEASE, CONTAINING SAME AS ACTIVE INGREDIENT

CROSS REFERENCE TO RELATED APPLICATIONS

This is the U.S. National Stage of International Application No. PCT/KR2017/007647, filed Jul. 17, 2017, which in turn claims the benefit of Korean Patent Application No. 10-2016-0089730, filed Jul. 15, 2016 and Korean Patent Application No. 10-2016-0089734, filed Jul. 15, 2016, all of which are incorporated herein in their entirety.

BACKGROUND OF THE INVENTION

1. Field of the Invention

The present invention relates to a novel organic sulfur compound, a method for preparing the same, and a pharmaceutical composition for preventing or treating cancer or inflammatory diseases, containing the same as an active ingredient.

2. Description of the Related Art

Organic sulfur (organosulfur) compounds are organic compounds that contain sulfur, which exist in various forms in the nature. In particular, the genus *Allium* such as garlic or onion contains various kinds of organic sulfur compounds, which display various physiological activities including anti-cancer activity, anti-inflammation activity and anti-bacterial activity (Organosulfur compounds and cancer, Lee M A, Advances in Experimental Medicine and Biology, 1996, 401,147-54 (1996)). Garlic contains alliin which is a precursor of organic sulfur compounds. In the process of cooking garlic, allicin is produced by the action of alliinase, and various kinds of organic sulfur compounds such as allyl sulfide, polysulfide and Ajoene are produced through continuous conversion process.

Among the organic sulfur compounds generated from garlic, Ajoene is relatively stable and contains allyl sulfoxide and vinyl disulfide.

Ajoene has been reported to have anti-cancer, anti-bacterial, anti-fungal, and anti-hypertrophic activities along with platelet aggregation inhibitory activity and induce apoptosis in human promyeloleukemic cells. It has also been reported that diallyl disulfide (DADS), one of the organic sulfur compounds of garlic, and allyl mercaptan (AM), the metabolism thereof, can suppress the proliferation of cancer cells by inhibiting histone deacetylase (HDAC).

Histone deacetylase is an enzyme that regulates the balance of acetylation and deacetylation of histone and non-histone proteins by promoting the hydrolysis of ε-amide bonds of lysine residues, by which the enzyme plays an important role in gene expression and differentiation, and maintains homeostasis of cells (Genes Dev, 2000, 14, 55; Expert Rev. Anticancer Ther. 2010, 10, 935; Am. J. Trans. Res, 2011, 3, 166). The over-expression of HDAC in various cancer cells causes the inhibition of major growth inhibition genes and thus has a mechanism to promote cancer cell proliferation. Therefore, HDAC has been a major target of anticancer agent development, and the development of an inhibitor thereof has been actively undergoing.

HDAC is also an important target of anti-inflammatory drug development since it plays an important role in the production of various inflammatory cytokines and in the immunomodulation. According to previous reports, HDAC is involved in inflammatory response by binding to p65 (RelA), one of the subunits of NF-κB. It has been reported that organic sulfur compounds inhibit the NF-κB activation induced by TNF-α (HDAC inhibition prevents NF-kB activation by suppressing proteasome activity: Down-regulation of proteasome subunit expression stabilizes IkBa, Biochemical Pharmacology 70 (2005) 394-406) and reduce the expression of inflammatory factors mediated by TLR (Toll-like receptor) (Histone deacetylase inhibitors decrease Toll-like receptor-mediated activation of proinflammatory gene expression by impairing transcription factor recruitment, Immunology, 122, 596-606). In addition, organic sulfur compounds can inhibit the activity of dendritic cells (DCs), a major regulator of immune response, at a low concentration, suggesting that they have the potential to be developed as a therapeutic agent for immune disease. DCs trigger innate immune responses through TLRs and induce acquired immune responses by regulating T cell responses (Histone deacetylase inhibition modulates indoleamine 2,3-dioxygenase-dependent DC functions and regulates experimental graft versus host disease in mice", Clin. Invest. 118(7): 2562-2573 (2008).

Particularly, inflammatory bowel disease is a representative chronic inflammatory disease that is an abnormal immune response to intestinal microorganisms. Epigenetic modulation such as HDAC is considered to be an important therapeutic strategy.

Until now, studies on the cancer cell proliferation inhibition mechanism of various organic sulfur compounds including Ajoene and the development of anticancer drugs based thereon have been continued. However, the results are only to confirm the cancer cell proliferation inhibition mechanism (The garlic compound Ajoene targets protein folding in the endoplasmic reticulum of cancer cells, KAS-CHULA et al., Molecular).

Various HDAC inhibitors have been developed for the purpose of treating cancer and have been clinically tested. Until now, 4 HDAC inhibitors (Vorinostat, Belinostat, Panobinostat and Romidepsin) have been approved by FDA (WO/2009/065926) to treat skin T cell lymphoma (CTCL) and peripheral T cell lymphoma (PTCL). About 20 promising HDAC inhibitors are in clinical or preclinical stages for cancer treatment, but most HDAC inhibitors have been shown to cause many side effects including fatigue, nausea, vomiting and cardiotoxicity. Such side effects seem to be attributed to lack of isozyme selectivity of HDAC. Therefore, a selective inhibitor is required in order to overcome the problem of lack of selectivity above. The development of HDAC selective inhibitor still stays in the early stage, and the development of HDAC 8 selective inhibitor has never been reported before.

Recent studies have shown that SAHA, the most representative organic sulfur compound, alleviates inflammation and reduces release of proinflammatory cytokines in the inflammatory bowel disease animal model (Selective histone deacetylase isoforms as potential therapeutic targets in inflammatory bowel diseases, Aliment Pharmacol Ther, 41, 26-38 (2015); Inhibition of histone deacetylases in inflammatory bowel diseases, Mol Med. 17(5-6):426-33 (2011)). Also, SAHA can protect mitochondrial functions of muscle cells by inhibiting the expression of HDAC 6 gene and the activity of the protein, suggesting that it has the effect of preventing and treating autoimmune myositis (Korean Patent Laid-Open No. 10-2016-0047657). Since various isoforms of HDAC are involved in the regulation of inflammatory cytokines and immunoinflammatory responses, studies on the development of organic sulfur compounds for the treatment of inflammatory bowel diseases have been conducted. However, the development of anti-inflammatory drugs is still in the early stage, and therefore continuous efforts are required.

Therefore, the present inventors have studied to develop a compound that has improved pharmaceutical efficacy and selectivity and at the same time has excellent anti-cancer, anti-inflammatory properties. In the course of our study, the present inventors developed a novel HDAC inhibitor and confirmed that the novel HDAC inhibitor of the invention was able to inhibit HDACs 1, 6 and 8 in a concentration of nanomolar or micromolar units and further was able to target HDAC 8 selectively, and also the inhibitor demonstrated a satisfactory pharmaceutical effect with less side effects so that it had potential for being used as a pharmaceutical composition for the prevention or treatment of cancer, leading to the completion of the present invention.

SUMMARY OF THE INVENTION

It is an object of the present invention to provide a novel organic sulfur compound.

It is another object of the present invention to provide a preparation method of the organic sulfur compound above.

It is further an object of the present invention to provide a pharmaceutical composition comprising the organic sulfur compound above as an active ingredient for the prevention or treatment of cancer.

It is also an object of the present invention to provide a heath functional food composition comprising the organic sulfur compound above as an active ingredient for preventing or ameliorating cancer.

It is also an object of the present invention to provide a pharmaceutical composition comprising the organic sulfur compound above as an active ingredient for the prevention or treatment of inflammatory diseases.

In addition, the present invention to provide a heath functional food composition comprising the organic sulfur compound above as an active ingredient for preventing or ameliorating inflammatory diseases.

To achieve the above objects, the present invention provides a compound represented by formula 1 below, a stereoisomer thereof or a pharmaceutically acceptable salt thereof.

[Formula 1]

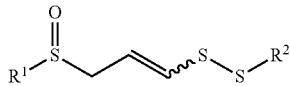

In formula 1 above,
$R^1$ is nonsubstituted or substituted phenyl,
wherein, the substituted phenyl can be substituted with one or more substitutents selected from the group consisting of hydroxy, amine, nitro, cyano, halogen, allyl, nonsubstituted or substituted $C_{1-5}$ straight or branched alkyl, and nonsubstituted or substituted $C_{1-5}$ straight or branched alkoxy, wherein, the substituted alkyl and the substituted alkoxy can be independently substituted with one or more substitutents selected from the group consisting of hydroxy, halogen, amine, nitro and cyano;

$R^2$ is nonsubstituted or substituted $C_{2-6}$ straight or branched alkenyl, nonsubstituted or substituted $C_{1-5}$ straight or branched alkyl, nonsubstituted or substituted $C_{1-5}$ straight or branched alkoxy, or nonsubstituted or substituted $C_{1-3}$alkyl$C_{6-10}$aryl, wherein, the substituted alkenyl, the substituted alkyl, the substituted alkoxy and the substituted alkylaryl can be independently substituted with one or more substitutents selected from the group consisting of hydroxy, halogen, amine, nitro, cyano, nonsubstituted or substituted $C_{1-3}$ straight or branched alkyl and nonsubstituted or substituted $C_{1-3}$ straight or branched alkoxy.

The present invention also provides a preparation method of the compound represented by formula 1 comprising the following steps, as shown in reaction formula 1 below:

preparing the compound represented by formula 3 from the compound represented by formula 2 (step 1);

preparing the compound represented by formula 4 from the compound represented by formula 3 prepared in step 1 above (step 2);

preparing the compound represented by formula 5 by reacting the compound represented by formula 4 prepared in step 2 above with p-TolSO$_2$SR$^2$ (para-toluenesulfonyl-SR$^2$) (step 3); and preparing the compound represented by formula 1 from the compound represented by formula 5 prepared in step 3 above (step 4).

[Reaction Formula 1]

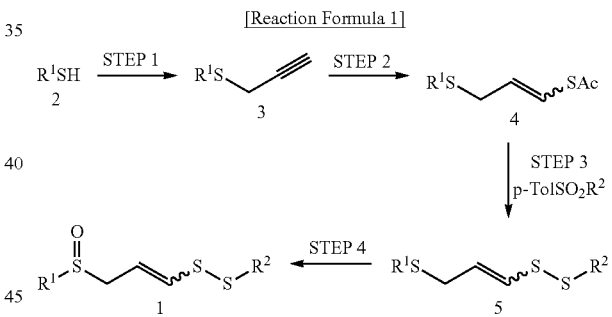

In reaction formula 1 above,
$R^1$ and $R^2$ are as defined in the formula 1.

The present invention also provides a pharmaceutical composition comprising the compound represented by formula 1 above, the stereoisomer thereof or the pharmaceutically acceptable salt thereof as an active ingredient for the prevention or treatment of cancer.

The present invention also provides a health functional food composition comprising the compound represented by formula 1 above, the stereoisomer thereof or the pharmaceutically acceptable salt thereof as an active ingredient for preventing or ameliorating cancer.

The present invention also provides a pharmaceutical composition comprising the compound represented by formula 1 above, the stereoisomer thereof or the pharmaceutically acceptable salt thereof as an active ingredient for the prevention or treatment of inflammatory diseases.

In addition, the present invention provides a health functional food composition comprising the compound represented by formula 1 above, the stereoisomer thereof or the pharmaceutically acceptable salt thereof as an active ingredient for preventing or ameliorating inflammatory diseases.

Advantageous Effect

The novel organic sulfur compound according to the present invention is capable of excellently inhibiting histone deacetylases (HDAC), particularly HDACs 1, 6 and 8 in a concentration of nanomolar or micromolar units and has been found to have an excellent effect against inflammatory diseases such as inflammatory bowel disease, and thus can be usefully used as a pharmaceutical composition for the prevention or treatment of inflammatory diseases, containing the same as an active ingredient.

In addition, particularly, the novel organic sulfur compound according to the present invention is capable of excellently inhibiting HDAC 8 in a concentration of nanomolar or micromolar units selectively, and has been found to be capable of inhibiting the proliferation of a renal cancer cell line (ACHN), a breast cancer cell line (MDA-MB-231), a colorectal cancer cell line (HCT-15), a prostate cancer cell line (PC-3), a gastric cancer cell line (NUGC-3) and a lung cancer cell line (NCl-H23), and thus can be usefully used for a pharmaceutical composition for the prevention or treatment of cancer, containing the same as an active ingredient.

DESCRIPTION OF THE PREFERRED EMBODIMENTS

Figure 1:
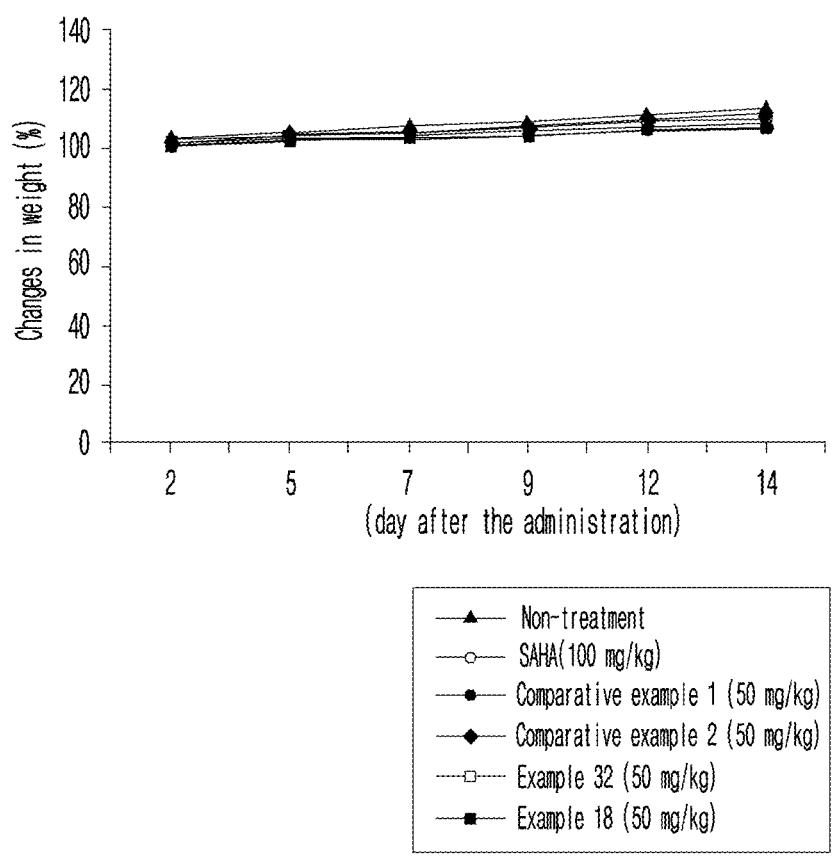
FIG. 1 is a graph illustrating the changes in weight of mice according to the non-treatment and the administration of SAHA (Vorinostat, 100 mg/kg), the compounds of comparative examples 1 and 2 (Ajoene, 50 mg/kg) and the compounds of examples 18 and 32 (50 mg/kg) (measured from day 2 to day 14 after the administration).

Hereinafter, the present invention is described in detail.

The present invention provides a compound represented by formula 1 below, a stereoisomer thereof or a pharmaceutically acceptable salt thereof.

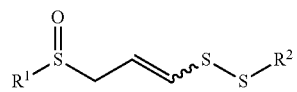

[Formula 1]

In formula 1 above, $R^1$ is nonsubstituted or substituted phenyl, wherein, the substituted phenyl can be substituted with one or more substitutents selected from the group consisting of hydroxy, amine, nitro, cyano, halogen, allyl, nonsubstituted or substituted $C_{1-5}$ straight or branched alkyl, and nonsubstituted or substituted $C_{1-5}$ straight or branched alkoxy, wherein, the substituted alkyl and the substituted alkoxy can be independently substituted with one or more substitutents selected from the group consisting of hydroxy, halogen, amine, nitro and cyano;

$R^2$ is nonsubstituted or substituted $C_{2-6}$ straight or branched alkenyl, nonsubstituted or substituted $C_{1-5}$ straight or branched alkyl, nonsubstituted or substituted $C_{1-5}$ straight or branched alkoxy, or nonsubstituted or substituted $C_{1-3}$alkyl$C_{6-10}$aryl, wherein, the substituted alkenyl, the substituted alkyl, the substituted alkoxy and the substituted alkylaryl can be independently substituted with one or more substitutents selected from the group consisting of hydroxy, halogen, amine, nitro, cyano, nonsubstituted or substituted $C_{1-3}$ straight or branched alkyl and nonsubstituted or substituted $C_{1-3}$ straight or branched alkoxy.

Preferably, $R^1$ is nonsubstituted or substituted phenyl, wherein, the substituted phenyl can be substituted with one or more substitutents selected from the group consisting of hydroxy, halogen, nonsubstituted or substituted $C_{1-3}$ straight or branched alkyl, and nonsubstituted or substituted $C_{1-3}$ straight or branched alkoxy, wherein, the substituted alkyl and the substituted alkoxy can be independently substituted with one or more substitutents selected from the group consisting of hydroxy, halogen, amine, nitro and cyano.

Preferably, $R^2$ is allyl, nonsubstituted or substituted $C_{1-3}$ straight or branched alkyl, or nonsubstituted or substituted benzyl, wherein, the substituted alkyl and the substituted benzyl can be independently substituted with one or more substitutents selected from the group consisting of hydroxy, halogen, amine, nitro, cyano, nonsubstituted or substituted $C_{1-3}$ straight or branched alkyl and nonsubstituted or substituted $C_{1-3}$ straight or branched alkoxy.

More preferably, $R^1$ is

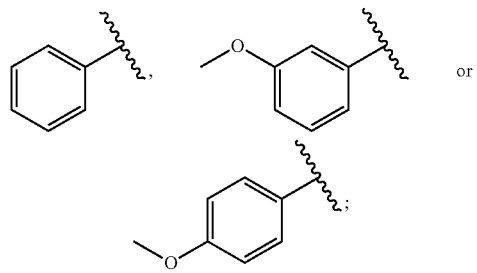

and
R² is

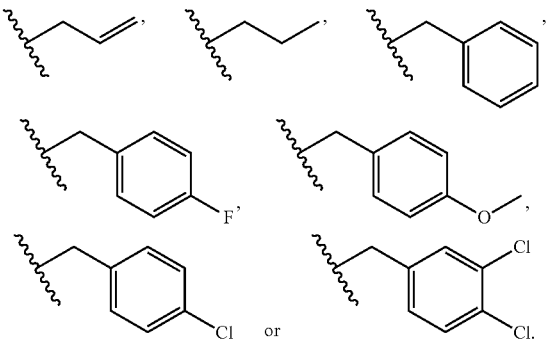

Preferable examples of the compound represented by formula 1 according to the present invention include the following compounds.
(1) (E)-1-allyl-2-(3-(phenylsulfinyl)prop-1-enyl)disulfane;
(2) (Z)-1-allyl-2-(3-(phenylsulfinyl)prop-1-enyl)disulfane;
(3) (E)-1-(3-(phenylsulfinyl)prop-1-enyl)-2-propyldisulfane;
(4) (Z)-1-(3-(phenylsulfinyl)prop-1-enyl)-2-propyldisulfane;
(5) (E)-1-benzyl-2-(3-(phenylsulfinyl)prop-1-enyl)disulfane;
(6) (Z)-1-benzyl-2-(3-(phenylsulfinyl)prop-1-enyl)disulfane;
(7) (E)-1-(4-fluorobenzyl)-2-(3-(phenylsulfinyl)prop-1-enyl)disulfane;
(8) (Z)-1-(4-fluorobenzyl)-2-(3-(phenylsulfinyl)prop-1-enyl)disulfane;
(9) (E)-1-(4-methoxybenzyl)-2-(3-(phenylsulfinyl)prop-1-enyl)disulfane;
(10) (Z)-1-(4-methoxybenzyl)-2-(3-(phenylsulfinyl)prop-1-enyl)disulfane;
(11) (E)-1-(4-chlorobenzyl)-2-(3-(phenylsulfinyl)prop-1-enyl)disulfane;
(12) (Z)-1-(4-chlorobenzyl)-2-(3-(phenylsulfinyl)prop-1-enyl)disulfane;
(13) (E)-1-(3,4-dichlorobenzyl)-2-(3-(phenylsulfinyl)prop-1-enyl)disulfane;
(14) (Z)-1-(3,4-dichlorobenzyl)-2-(3-(phenylsulfinyl)prop-1-enyl)disulfane;
(15) (E)-1-allyl-2-(3-(3-methoxyphenylsulfinyl)prop-1-enyl)disulfane;
(16) (Z)-1-allyl-2-(3-(3-methoxyphenylsulfinyl)prop-1-enyl)disulfane;
(17) (E)-1-(3-(3-methoxyphenylsulfinyl)prop-1-enyl)-2-propyldisulfane;
(18) (Z)-1-(3-(3-methoxyphenylsulfinyl)prop-1-enyl)-2-propyldisulfane;
(19) (E)-1-benzyl-2-(3-(3-methoxyphenylsulfinyl)prop-1-enyl)disulfane;
(20) (Z)-1-benzyl-2-(3-(3-methoxyphenylsulfinyl)prop-1-enyl)disulfane;
(21) (E)-1-(4-fluorobenzyl)-2-(3-(3-methoxyphenylsulfinyl)prop-1-enyl)disulfane;
(22) (Z)-1-(4-fluorobenzyl)-2-(3-(3-methoxyphenylsulfinyl)prop-1-enyl)disulfane;
(23) (E)-1-(4-chlorobenzyl)-2-(3-(3-methoxyphenylsulfinyl)prop-1-enyl)disulfane;
(24) (Z)-1-(4-chlorobenzyl)-2-(3-(3-methoxyphenylsulfinyl)prop-1-enyl)disulfane;
(25) (E)-1-(3,4-dichlorobenzyl)-2-(3-(3-methoxyphenylsulfinyl)prop-1-enyl)disulfane;
(26) (Z)-1-(3,4-dichlorobenzyl)-2-(3-(3-methoxyphenylsulfinyl)prop-1-enyl)disulfane;
(27) (E)-1-allyl-2-(3-(4-methoxyphenylsulfinyl)prop-1-enyl)disulfane;
(28) (Z)-1-allyl-2-(3-(4-methoxyphenylsulfinyl)prop-1-enyl)disulfane;
(29) (E)-1-(3-(4-methoxyphenylsulfinyl)prop-1-enyl)-2-propyldisulfane;
(30) (Z)-1-(3-(4-methoxyphenylsulfinyl)prop-1-enyl)-2-propyldisulfane;
(31) (E)-1-benzyl-2-(3-(4-methoxyphenylsulfinyl)prop-1-enyl)disulfane;
(32) (Z)-1-benzyl-2-(3-(4-methoxyphenylsulfinyl)prop-1-enyl)disulfane;
(33) (E)-1-(4-fluorobenzyl)-2-(3-(4-methoxyphenylsulfinyl)prop-1-enyl)disulfane;
(34) (Z)-1-(4-fluorobenzyl)-2-(3-(4-methoxyphenylsulfinyl)prop-1-enyl)disulfane;
(35) (E)-1-(4-chlorobenzyl)-2-(3-(4-methoxyphenylsulfinyl)prop-1-enyl)disulfane;
(36) (Z)-1-(4-chlorobenzyl)-2-(3-(4-methoxyphenylsulfinyl)prop-1-enyl)disulfane;
(37) (E)-1-(3,4-dichlorobenzyl)-2-(3-(4-methoxyphenylsulfinyl)prop-1-enyl)disulfane; and
(38) (Z)-1-(3,4-dichlorobenzyl)-2-(3-(4-methoxyphenylsulfinyl)prop-1-enyl)disulfane.

The present inventors completed this invention by confirming the anti-cancer activity and the anti-inflammatory activity of the organic sulfur compound of the present invention.

The compound represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, and phosphorous acid; non-toxic organic acids such as aliphatic mono/dicarboxylate, phenyl-substituted alkanoate, hydroxy alkanoate, alkandioate, aromatic acids, and aliphatic/aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salts are exemplified by sulfate, pyrosulfate, bisulfate, sulphite, bisulphite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutylate, caprate, heptanoate, propiolate, oxalate, malonate, succinate, suberate, cabacate, fumarate, maliate, butyne-1,4-dioate, hexane-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, hydroxybutylate, glycolate, malate, tartrate, methanesulfonate, propanesulfonate, naphthalene-1-sulfonate, naphthalene-2-sulfonate, and mandelate.

The acid addition salt in this invention can be prepared by the conventional method known to those in the art. For example, the derivative represented by formula 1 is dissolved in an organic solvent such as methanol, ethanol, acetone, dichloromethane, and acetonitrile, to which organic acid or inorganic acid is added to induce precipitation. Then, the precipitate is filtered and dried to give the salt. Or the solvent and the excessive acid are distillated under reduced pressure, and dried to give the salt. Or the precipitate is crystallized in an organic solvent to give the same.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with proper silver salt (ex; silver nitrate).

The present invention includes not only the compound represented by formula 1 but also a pharmaceutically acceptable salt thereof, and a solvate, a stereoisomer, or a hydrate possibly produced from the same.

The present invention also provides a preparation method of the compound represented by formula 1 comprising the following steps, as shown in reaction formula 1 below:

preparing the compound represented by formula 3 from the compound represented by formula 2 (step 1);

preparing the compound represented by formula 4 from the compound represented by formula 3 prepared in step 1 above (step 2);

preparing the compound represented by formula 5 by reacting the compound represented by formula 4 prepared in step 2 above with p-TolSO$_2$SR$^2$ (para-toluenesulfonyl-SR$^2$) (step 3); and preparing the compound represented by formula 1 from the compound represented by formula 5 prepared in step 3 above (step 4).

[Reaction Formula 1]

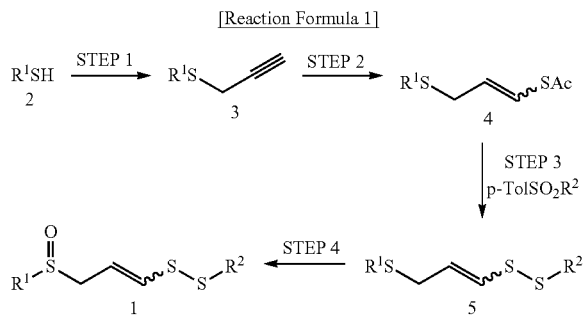

In reaction formula 1 above,

R$^1$ and R$^2$ are as defined in the formula 1.

Hereinafter, the preparation method of the compound represented by formula 1 of the present invention shown in reaction formula 1 above will be described in more detail, step by step.

In the preparation method of the compound represented by formula 1 of the present invention shown in reaction formula 1 above, step 1 is to prepare the compound represented by formula 3 from the compound represented by formula 2.

At this time, step 1 above can be understood as a propargylation reaction. This reaction is carried out by adding propargyl halide from thiol R$^1$SH or the corresponding isothiouronium salt (R$^1$SC(¼NH$_2$)NH$_2$ þ Br), but not always limited thereto. In the reaction above, the reaction temperature is 10~40° C. and more preferably 20~30° C., but not always limited thereto. The reaction time is 0.5~20 hours and more preferably 1~10 hours, but not always limited thereto. The conditions such as the reaction temperature and the reaction time can be varied according to the purpose of the experiment, and therefore any possible changes in the conditions above for the accomplishment of the purpose of the present invention can be included in the criteria of the present invention.

In the preparation method of the compound represented by formula 1 of the present invention shown in reaction formula 1 above, step 2 is to prepare the compound represented by formula 4 from the compound represented by formula 3 prepared in step 1 above.

At this time, step 2 above can be understood as a radical addition reaction. Particularly, step 2 is to prepare vinylthioacetate by adding a radical initiator and thioacetic acid to the compound prepared in step 1 in the form of a stereoisomeric mixture or as an individual isomer, but not always limited thereto. In the reaction above, the reaction temperature is 60~100° C. and more preferably 70~90° C., but not always limited thereto. The reaction time is not particularly limited as long as the reaction proceeds completely and the reaction product can be maximally converted. The conditions such as the reaction temperature and the reaction time can be varied according to the purpose of the experiment, and therefore any possible changes in the conditions above for the accomplishment of the purpose of the present invention can be included in the criteria of the present invention.

In the preparation method of the compound represented by formula 1 of the present invention shown in reaction formula 1 above, step 3 is to prepare the compound represented by formula 5 by reacting the compound represented by formula 4 prepared in step 2 above with p-TolSO$_2$SR$^2$ (para-toluenesulfonyl-SR$^2$).

At this time, step 3 above can be understood as a sulfenylation reaction to vinyldisulfide. Particularly, step 3 is to prepare vinyldisulfide, the target compound, by adding S-allyl p-toluenesulfonylthioate or a corresponding compound thereof to the compound prepared in step 2, but not always limited thereto. In the reaction above, the reaction temperature is -20~10° C. and more preferably -10~0° C., which is the temperature for the progress of the reaction. When each compound is added, it is more preferred to lower the temperature to -30~-90° C. by using liquid nitrogen, liquid nitrogen/acetone nitrile or liquid nitrogen/acetone, but not always limited thereto. The reaction time is not particularly limited as long as the reaction proceeds completely and the reaction product can be maximally converted. For example, the reaction time is preferably 0.5~10 hours and more preferably 1~5 hours, but not always limited thereto. The conditions such as the reaction temperature and the reaction time can be varied according to the purpose of the experiment, and therefore any possible changes in the conditions above for the accomplishment of the purpose of the present invention can be included in the criteria of the present invention.

In the preparation method of the compound represented by formula 1 of the present invention shown in reaction formula 1 above, step 4 is to prepare the compound represented by formula 1 from the compound represented by formula 5 prepared in step 3 above.

At this time, step 4 above can be understood as an oxidation reaction. Particularly, step 3 is to prepare the final target compound by adding m-CPBA or a corresponding compound thereof to the compound prepared in step 3 in the form of an E/Z mixture or a single stereoisomer, but not always limited thereto. In the reaction above, the reaction temperature is 0~30° C. and more preferably 10~20° C. When each compound is added, it is more preferred to lower the temperature to −30~−90° C. by using liquid nitrogen, liquid nitrogen/acetone nitrile or liquid nitrogen/acetone. After the addition of the compound, the reaction can be induced while the temperature is slowly raised to room temperature for several hours, but not always limited thereto. The reaction time is not particularly limited as long as the reaction proceeds completely and the reaction product can be maximally converted. The conditions such as the reaction temperature and the reaction time can be varied according to the purpose of the experiment, and therefore any possible changes in the conditions above for the accomplishment of the purpose of the present invention can be included in the criteria of the present invention.

The preparation method of the present invention described above can be accomplished preferably in accordance with the following preparative examples and examples, but they are only examples for specific explanations of the present invention and thus the present invention is not limited thereto.

The present invention also provides a pharmaceutical composition comprising the compound represented by formula 1 above, the stereoisomer thereof or the pharmaceutically acceptable salt thereof as an active ingredient for the prevention or treatment of cancer.

At this time, the compound represented by formula 1 above is characterized by preventing or treating cancer by inhibiting HDAC (histone deacetylase), suggesting that the compound can inhibit cancer proliferation by inhibiting the mechanism of histone deacetylase.

Particularly, HDAC (histone deacetylase) is an enzyme that regulates the balance of acetylation and deacetylation of histone and non-histone proteins by promoting the hydrolysis of ε-amide bonds of lysine residues, by which the enzyme plays an important role in gene expression and differentiation, and maintains homeostasis of cells The overexpression of HDAC in various cancer cells causes the inhibition of major growth inhibition genes and thus accelerates cancer cell proliferation. The compound represented by formula 1 according to the present invention, the stereoisomer thereof or the pharmaceutically acceptable salt thereof is capable of inhibiting the above-mentioned mechanisms and so that inhibit cancer cell proliferation characteristically.

In the meantime, the cancer herein is at least one selected from the group consisting of pseudomyxoma, intrahepatic cholangiocarcinoma, liver cancer, thyroid cancer, colon cancer, testicular cancer, myelodysplastic syndrome, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, small cell lung cancer, pediatric brain cancer, pediatric lymphoma, childhood leukemia, small bowel cancer, meningioma, esophagus cancer, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblatic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, pancreatic cancer, salivary gland cancer, Kaposi's sarcoma, Paget's disease, tonsil cancer, squamous cell carcinoma, adenocarcinoma of lung, lung cancer, squamous cell carcinoma of lung, skin cancer, anal cancer, rhabdomyosarcoma, laryngeal cancer, pleural cancer, and thymus cancer, and more preferably selected from the group consisting of kidney cancer, breast cancer, colon cancer, prostate cancer, gastric cancer, lung cancer, and pediatric cancer.

The present invention also provides a health functional food composition comprising the compound represented by formula 1 above, the stereoisomer thereof or the pharmaceutically acceptable salt thereof as an active ingredient for preventing or ameliorating cancer.

At this time, the compound represented by formula 1 above is characterized by preventing or treating cancer by inhibiting HDAC (histone deacetylase), suggesting that the compound can inhibit cancer proliferation by inhibiting the mechanism of histone deacetylase.

Particularly, HDAC (histone deacetylase) is an enzyme that regulates the balance of acetylation and deacetylation of histone and non-histone proteins by promoting the hydrolysis of ε-amide bonds of lysine residues, by which the enzyme plays an important role in gene expression and differentiation, and maintains homeostasis of cells The overexpression of HDAC in various cancer cells causes the inhibition of major growth inhibition genes and thus accelerates cancer cell proliferation. The compound represented by formula 1 according to the present invention, the stereoisomer thereof or the pharmaceutically acceptable salt thereof is capable of inhibiting the above-mentioned mechanisms and so that inhibit cancer cell proliferation characteristically.

The present invention also provides a pharmaceutical composition comprising the compound represented by formula 1 above, the stereoisomer thereof or the pharmaceutically acceptable salt thereof as an active ingredient for the prevention or treatment of inflammatory diseases.

At this time, the compound represented by formula 1 above is characterized by preventing or treating cancer by inhibiting HDAC (histone deacetylase), suggesting that the compound can inhibit inflammatory diseases by inhibiting the mechanism of histone deacetylase.

Particularly, the compound represented by formula 1 above, the stereoisomer thereof or the pharmaceutically acceptable salt thereof according to the present invention can inhibit the mechanism of promoting inflammatory response induced by the over-expression of HDAC.

In the meantime, the inflammatory disease herein is at least one selected from the group consisting of dermatitis, allergy, atopy, asthma, conjunctivitis, rhinitis, otitis, sore throat, tonsillitis, pneumonia, gastric ulcer, gastritis, Crohn's disease, inflammatory bowel disease, lupus, hepatitis, cystitis, nephritis, Sjogren's syndrome, multiple sclerosis, and acute and chronic inflammatory diseases.

In addition, the present invention provides a health functional food composition comprising the compound represented by formula 1 above, the stereoisomer thereof or the pharmaceutically acceptable salt thereof as an active ingredient for preventing or ameliorating inflammatory diseases.

The following experiment was performed to evaluate the cancer proliferation inhibitory activity of the compound represented by formula 1 above, the stereoisomer thereof or the pharmaceutically acceptable salt thereof according to the present invention.

First, the cancer proliferation inhibitory activity ($GI_{50}$) was evaluated in human cancer cell lines (renal cancer cell line (ACHN), breast cancer cell line (MDA-MB-231), colorectal cancer cell line (HCT-15), prostate cancer cell line (PC-3), gastric cancer cell line (NUGC-3) and lung cancer cell line (NCl-H23)). As a result, it was confirmed that the cancer proliferation inhibitory effect of the compound of the present invention was superior to that of Ajoene. In particular, the compound represented by formula 1 wherein $R^1$ was phenyl demonstrated more excellent cancer proliferation inhibitory effect than not only Ajoene but also the compound wherein $R^1$ was benzyl or allyl (see experimental example 1-1).

Therefore, the present inventors additionally synthesized a derivative of the compound represented by formula 1 wherein $R^1$ is phenyl, followed by the same investigation of cancer proliferation inhibitory effect. As a result, when the $3^{rd}$ or $4^{th}$ site of phenyl was substituted with methoxy, a better cancer proliferation activity was confirmed than when $R^1$ was phenyl (see experimental example 1-2).

After the experiments described above, the present inventors evaluated the inhibitory activity ($IC_{50}$) against HDAC 1, 6, and 8 in order to confirm the HDAC enzyme inhibitory activity of the phenyl-based derivative.

At this time, the cancer proliferation inhibitory activity of the conventional HDAC targeting anticancer agent SAHA (Vorinostat) was compared as a percentage as a control. As a result, it was confirmed that the phenyl-based derivative according to the present invention exhibited better HDAC inhibitory activity than Ajoene and SAHA.

In particular, the novel organic sulfur compound according to the present invention was confirmed to have 30 to 100-fold higher HDAC 8 inhibitory activity than HDAC 1 and HDAC 6 inhibitory activity. Compared with the control SAHA, the HDAC inhibitory activity of the novel organic sulfur compound of the present invention was 161.9% by the control. The present inventors completed this invention by confirming the above (see experimental example 2).

As a part of in vivo experiments, an experiment was performed to evaluate the cancer proliferation inhibitory activity in the mice xenotransplanted with prostate cancer. As a result, the novel organic sulfur compound according to the present invention was confirmed to be able to inhibit cancer cell proliferation efficiently (see experimental example 3).

The anti-inflammatory activity of the novel organic sulfur compound according to the present invention was confirmed by evaluating the HDAC enzyme inhibitory activity. As shown in experimental example 2 below, the compound of the present invention was able to inhibit HDAC 1, 6, and 8 better than Ajoene. In particular, the HDAC 8 inhibitory activity was approximately 30-100 times higher than the HDAC 1 and HDAC 6 inhibitory activity. The HDAC 8 inhibitory activity of the novel compound of the present invention was higher than that of SAHA (Vorinostat). Therefore, it was confirmed that the novel organic sulfur compound according to the present invention exhibited an excellent anti-inflammatory activity, leading to the completion of the present invention (see experimental example 2).

Practical and presently preferred embodiments of the present invention are illustrative as shown in the following Examples.

However, it will be appreciated that those skilled in the art, on consideration of this disclosure, may make modifications and improvements within the spirit and scope of the present invention.

<Preparation Method> Preparation of Para-Toluenesulfonyl-$SR^2$ $R^2X$ (X=¼Cl or Br; 1.0 eq) was dissolved in DMF (1 M) solution containing potassium p-toluenethiosulfonate (1.3 eq) dissolved therein without using a solvent or dissolved in DMF, which was slowly added to the solution by using a syringe. The reaction mixture was stirred at room temperature for 3 hours or heated with observing the conversion of $R^2C$ by TLC. The reaction was terminated by saturated $NaHCO_3$ aqueous solution. The obtained mixture was extracted with dichloromethane. The organic extract was dried over magnesium sulfate. The solvent was eliminated under reduced pressure and the residue was purified by silica gel column chromatography using hexane/ethyl acetate. As a result, a target compound was obtained.

<Preparative Example 1> Toluene-4-thiosulfonic Acid, S-2-propene-1-ylester

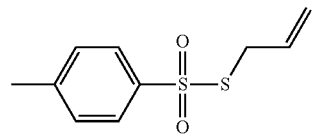

Yield form: light yellow oil (90.7%); $R_f$=0.34 (n-hexane/Ethyl acetate 10:1); $^1H$ NMR (400 MHz, $CDCl_3$) δ 7.48 (2H, d, J=8.4 Hz), 7.27 (2H, d, J=8.4 Hz), 5.57-5.67 (1H, m), 5.09-5.14 (1H, m), 4.99-5.03 (2H, m), 3.57-3.59 (2H, m), 2.36 (3H, s); $^{13}C$ NMR (100 MHz, $CDCl_3$) δ 144.4, 141.4, 130.1, 129.3, 126.5, 119.6, 38.3, 21.3.

<Preparative Example 2> Toluene-4-thiosulfonic Acid, S-propylester

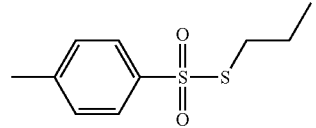

Yield form: light yellow oil (80.5%); $R_f$=0.29 (n-hexane/Ethyl acetate 10:1); $^1H$ NMR (400 MHz, $CDCl_3$) δ 7.81 (2H, d, J=8.4 Hz), 7.24 (2H, d, J=8.4 Hz), 2.96 (2H, t, J=7.2 Hz), 2.45 (3H, s), 1.58-1.68 (2H, m), 0.92 (3H, t, J=7.2 Hz); $^{13}C$ NMR (100 MHz, $CDCl_3$) δ 144.7, 142.0, 129.8, 126.9, 37.9, 22.1, 21.6, 13.1.

<Preparative Example 3> Toluene-4-thiosulfonic Acid, S-benzylester

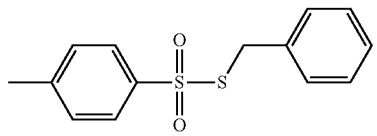 [SMILES: Cc1ccc(S(=O)(=O)SCc2ccccc2)cc1]

Yield form: white solid (96.4%); $R_f$=0.36 (n-hexane/Ethyl acetate 10:1); $^1$H NMR (400 MHz, CDCl$_3$) δ 7.72 (2H, d J=8.4 Hz), 7.26 (2H, d J=8.4 Hz), 7.20-7.23 (3H, m), 7.16-7.18 (2H, m), 4.24 (2H, s), 2.42 (3H, s); $^{13}$C NMR (100 MHz, CDCl$_3$) δ 144.6, 141.9, 133.7, 129.7, 129.1, 128.8, 127.9, 126.9, 40.3, 21.6.

<Preparative Example 4> Toluene-4-thiosulfonic Acid, S-(4-fluoro-benzyl) ester

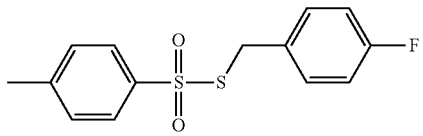 [SMILES: Cc1ccc(S(=O)(=O)SCc2ccc(F)cc2)cc1]

Yield form: white solid (89.5%); $R_f$=0.31 (n-hexane/Ethyl acetate 8:1); $^1$H NMR (400 MHz, CDCl$_3$) δ 7.69 (2H, dd, J=1.6, 6.8 Hz), 7.27 (2H, dd, J=1.6, 6.8 Hz), 7.13-7.17 (2H, m), 6.88-6.92 (2H, m), 4.22 (2H, s), 2.43 (3H, s); $^{13}$C NMR (100 MHz, CDCl3) δ 144.8, 141.9, 130.8, 130.7, 1209.7, 126.9, 115.8, 115.5, 39.5, 21.6

<Preparative Example 5> Toluene-4-thiosulfonic Acid, S-(4-methoxy-benzyl) ester

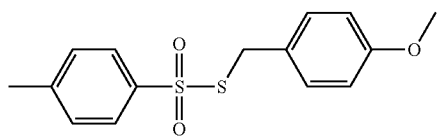

Yield form: white solid (63.0%); $R_f$=0.24 (n-hexane/Ethyl acetate 8:1); $^1$H NMR (400 MHz, CDCl$_3$) δ 7.69 (2H, dd, J=1.6, 8.4 Hz), 7.27 (2H, dd, J=1.6, 8.4 Hz), 7.13-7.17 (2H, m), 6.88-6.92 (2H, m), 4.22 (2H, s), 2.43 (3H, s); $^{13}$C NMR (100 MHz, CDCl3) δ 130.4, 129.7, 126.9, 114.2, 55.3, 39.9, 21.6.

<Preparative Example 6> Toluene-4-thiosulfonic Acid, S-(4-chloro-benzyl) ester

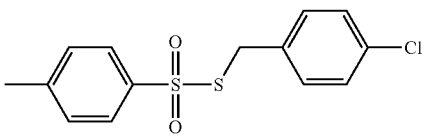 [SMILES: Cc1ccc(S(=O)(=O)SCc2ccc(Cl)cc2)cc1]

Yield form: light yellow oil (68.7%); $R_f$=0.24 (n-hexane/Ethyl acetate 8:1); $^1$H NMR (400 MHz, CDCl$_3$) δ 7.67 (2H, d, J=8.4 Hz), 7.25 (2H, d, J=8 Hz), 7.17 (1H, dd, J=2, 6.4 Hz), 7.10 (2H, d, J=8.8 Hz), 4.21 (2H, s), 2.43 (3H, s); $^{13}$C NMR (100 MHz, CDCl$_3$) δ 144.9, 142.1, 133.9, 132.6, 130.5, 129.8, 128.9, 127.0, 39.7, 21.7.

<Preparative Example 7> Toluene-4-thiosulfonic Acid, S-(3,4-dichloro-benzyl) ester

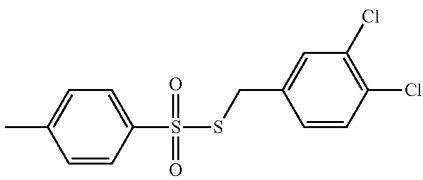 [SMILES: Cc1ccc(S(=O)(=O)SCc2ccc(Cl)c(Cl)c2)cc1]

Yield form: light yellow oil (78.9%); $R_f$=0.46 (n-hexane/Ethyl acetate 4:1); $^1$H NMR (400 MHz, CDCl$_3$) δ 7.62 (2H, dd, J=2, 6.8 Hz), 7.21~7.26 (3H, m), 7.14 (1H, d, J=2 Hz), 7.00 (1H, dd, =2.4, 8.4 Hz), 4.19 (2H, s), 2.42 (3H, s); $^{13}$C NMR (100 MHz, CDCl$_3$) δ 145.0, 141.9, 134.3, 132.5, 131.9, 130.8, 130.4, 129.6, 128.3, 126.9, 39.0, 21.6.

<Example 1> Preparation of (E)-1-allyl-2-(3-(phenylsulfinyl)prop-1-enyl)disulfane

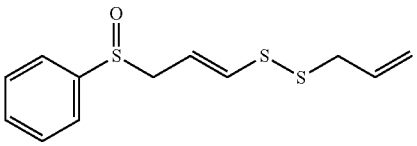 [SMILES: C=CCSS/C=C/CS(=O)c1ccccc1]

Step 1: Propargylation Reaction

Benzenethiol or the corresponding isothiouronium salt (Ph-SC(¼NH$_2$)NH$_2$ þ Br) was added to methanol (0.5 M) degassed at 0° C., to which solid KOH (1.2 eq by ethenethiol or 2.5 eq by the salt above) was added. 5 minutes later, propargyl bromide (1.5 eq, 80% in toluene) was added thereto. The resulting mixture was allowed to warm at room temperature. After several hours, the propargylation reaction was completed, confirmed by TLC. Methanol was eliminated under reduced pressure and the residue was extracted with water and ethyl acetate or dichloromethane (three times). The extract was dried and the solvent was eliminated under reduced pressure. The residue was purified by silica gel chromatography using toluene/hexane mixture. As a result, a target compound (propargylated sulfide) was obtained.

Step 2: Radical Addition Reaction

Degassed toluene (0.5 M) and AIBN or its corresponding radical initiator (5 mol %) was added to the compound prepared in step 1 above. The resulting mixture was heated to 85° C., to which thioacetic acid (1.1 eq) dissolved in toluene (1 M) was added dropwise for 1 hour. Then, the mixture was stirred until the reaction was completed, during which the progress of the reaction was observed by TLC. In some cases, thioacetic acid was added to complete the reaction fully and at this time the generation of a by-product was carefully watched. Upon completion of the reaction, the solvent was eliminated and the residue was purified by silica gel column chromatography using toluene or ethyl acetate/petroleum ether mixture. As a result, a target compound (vinylthioacetate) was obtained as a mixture of Z:E isomers (weight ratio 2:1).

Step 3: Sulfenylation to Vinyldisulfide

The compound prepared in step 2 above was dissolved in methanol (1 M), which was cooled down to −40° C. using a cooling bath of acetone nitrile/liquid nitrogen. KOH (1.05 eq, 1 M) dissolved in methanol was slowly added thereto by using a syringe. The obtained mixture was stirred for 20 minutes, followed by cooling to −78° C. using a cooling bath of acetone nitrile/liquid nitrogen. Methanol (1.1 eq, 1 M) containing the compound prepared in preparative example 1 dissolved therein was added thereto by using a syringe. The temperature of the mixture was raised to 0° C. The mixture was stirred for 2 hours, and then the reaction was terminated by using NH₄Cl aqueous solution. The organic product was extracted with ethyl acetate or dichloromethane (three times). The extract was dried and the solvent was eliminated. The residue was purified by column chromatography. As a result, a target compound (vinyldisulfide) was obtained.

Step 4: Oxidation Reaction

The compound prepared in step 3 was dissolved in dichloromethane (0.2 M). The mixture was cooled down to −78° C. in nitrogen atmosphere, to which m-CPBA (1.1 eq) was added. The reaction was allowed to proceed over several hours at room temperature until the reactant was confirmed to be exhausted by TLC (40% ethyl acetate/petroleum ether). The reaction was quenched with saturated NaHCO₃ aqueous solution and the product was extracted with ethyl acetate or dichloromethane (three times). The obtained organic layer was dried under reduced pressure and concentrated. The obtained residue was purified by silica gel column chromatography using petroleum ether/ethyl acetate mixture. As a result, a final target compound was obtained as an E/Z mixture. In some cases, the stereoisomer could be separated by gravity chromatography at a low flow rate and at this time the yield was varied from 60 to 90%. The reaction temperature for optimal conversion was different for each substrate.

1:2 cis:trans (46.5%, separable)

Yield form: yellow oil

Rf=0.27 (n-hexane/ethyl acetate=2:1); (E) 1H NMR (400 MHz, CD3OD+CDCl3) δ 7.56~7.66 (5H, m), 6.21 (1H, d, J=14.4 Hz), 5.64~5.81 (2H, m), 5.10~5.14 (1H, m), 5.10~5.14 (2H, m), 3.81~3.87 (1H, m), 3.65~3.70 (1H, m), 3.25~3.30 (2H, m).

<Example 2> Preparation of (Z)-1-allyl-2-(3-(phenylsulfinyl)prop-1-enyl)disulfane

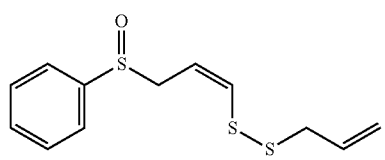 [SMILES: C=CCSS/C=C\CS(=O)c1ccccc1]

A target compound was obtained by the same manner as described in example 1 as a stereoisomer.

1:2 cis:trans (46.5%, separable)

Yield form: yellow oil

Rf=0.27 (n-hexane/ethyl acetate=2:1); (Z) 1H NMR (400 MHz, CD3OD+CDCl3) δ 7.58~7.69 (5H, m), 6.55 (1H, d, J=9.6 Hz), 5.76~5.86 (1H, m), 5.55~5.62 (1H, m), 5.13~5.20 (2H, m), 3.87~3.93 (1H, m), 3.75~3.81 (1H, m), 3.26~3.34 (2H, m).

<Example 3> Preparation of (E)-1-(3-(phenylsulfinyl)prop-1-enyl)-2-propyldisulfane

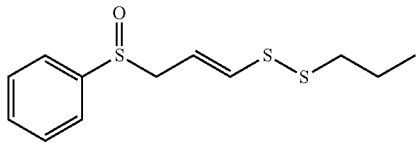 [SMILES: CCCSS/C=C/CS(=O)c1ccccc1]

A target compound was obtained by the same manner as described in example 1 except that the compound of preparative example 2 was used instead of the compound of preparative example 1 in step 3 of example 1.

2.5:1 cis:trans (56.6%, separable)

Yield form: yellow oil

Rf=0.27 (n-hexane/ethyl acetate=2:1); (E) 1H NMR (400 MHz, CD3OD) δ 7.58~7.64 (5H, m), 6.22 (1H, d, J=14.8 Hz), 5.64~5.72 (1H, m), 5.30~5.37 (2H, m), 3.81~3.87 (2H, m), 3.65~3.71 (2H, m), 2.60 (2H, t, J=7.2 Hz), 1.59~1.69 (2H, m), 0.97 (3H, t, J=7.2 Hz); 13C NMR (100 MHz, CD3OD) δ 136.1, 132.6, 130.4, 125.7, 59.3, 48.4, 40.8, 13.3.

<Example 4> Preparation of (Z)-1-(3-(phenylsulfinyl)prop-1-enyl)-2-propyldisulfane

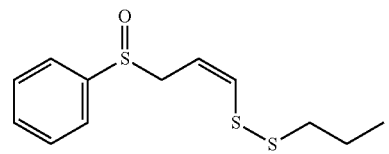 [SMILES: CCCSS/C=C\CS(=O)c1ccccc1]

A target compound was obtained by the same manner as described in example 3 as a stereoisomer.

2.5:1 cis:trans (56.6%, separable)

Yield form: yellow oil

Rf=0.27 (n-hexane/ethyl acetate=2:1); (Z) 1H NMR (400 MHz, CD3OD+CDCl3) δ 7.58~7.67 (5H, m), 6.54 (1H, d, J=9.2 Hz), 5.28~5.59 (1H, m), 3.86~3.91 (1H, m), 3.73~3.79 (1H, m), 2.62 (2H, t, J=7.2 Hz), 1.58~1.66 (2H, m), 0.96 (3H, t, J=7.2 Hz).

<Example 5> Preparation of (E)-1-benzyl-2-(3-(phenylsulfinyl)prop-1-enyl)disulfane

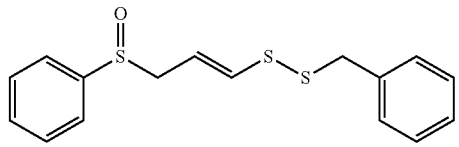 [SMILES: O=S(C/C=C/SSCc1ccccc1)c1ccccc1]

A target compound was obtained by the same manner as described in example 1 except that the compound of preparative example 3 was used instead of the compound of preparative example 1 in step 3 of example 1.

1:1 cis:trans (51.3%, separable)

Yield form: yellow oil

Rf=0.27 (n-hexane/ethyl acetate=2:1); (E) 1H NMR (400 MHz, CD3OD+CDCl3) δ 7.56~7.64 (5H, m), 7.23~7.7.31

(5H, m), 6.09 (1H, d, J=14.4 Hz), 5.56~5.64 (1H, m), 3.84 (2H, s), 3.73~3.79 (1H, m), 3.58~3.63 (1H, m); 13C NMR (100 MHz, CD3OD+CDCl3) δ 136.1, 133.6, 131.3, 129.7, 128.9, 128.5, 127.3, 119.2, 41.4, 36.5.

<Example 6> Preparation of (Z)-1-benzyl-2-(3-(phenylsulfinyl)prop-1-enyl)disulfane

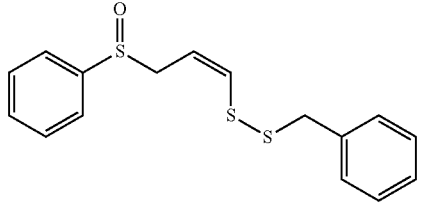 [SMILES: O=S(C/C=C\SSCc1ccccc1)c1ccccc1]

A target compound was obtained by the same manner as described in example 5 as a stereoisomer.
1:1 cis:trans (51.3%, separable)
Yield form: yellow oil
Rf=0.27 (n-hexane/ethyl acetate=2:1); (Z) 1H NMR (400 MHz, CD3OD+CDCl3) δ 7.57~7.64 (5H, m), 7.20~7.31 (5H, m), 6.21 (1H, d, J=9.6 Hz), 5.38~5.45 (1H, m), 3.86 (2H, s), 3.78~3.84 (1H, m), 3.67~3.72 (1H, m).

<Example 7> Preparation of (E)-1-(4-fluorobenzyl)-2-(3-(phenylsulfinyl)prop-1-enyl)disulfane

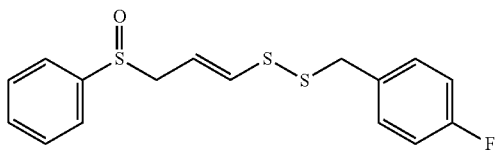 [SMILES: O=S(C/C=C/SSCc1ccc(F)cc1)c1ccccc1]

A target compound was obtained by the same manner as described in example 1 except that the compound of preparative example 4 was used instead of the compound of preparative example 1 in step 3 of example 1.
1:2 cis:trans (48.4%, separable)
Yield form: yellow oil
Rf=0.24 (n-hexane/ethyl acetate=2:1); (E) 1H NMR (400 MHz, CDCl3) δ 7.51~7.59 (5H, m), 7.20~7.23 (2H, m), 6.98~7.01 (2H, m), 5.98 (1H, d, J=14.4 Hz), 5.58~5.66 (1H, m), 3.81 (2H, s), 3.56~3.62 (1H, m), 3.44~3.49 (1H, m); 13C NMR (100 MHz, CDCl3) δ 134.3, 131.5, 131.4, 131.3, 129.4, 124.6, 116.6, 115.9, 115.7, 59.6, 41.7.

<Example 8> Preparation of (Z)-1-(4-fluorobenzyl)-2-(3-(phenylsulfinyl)prop-1-enyl)disulfane

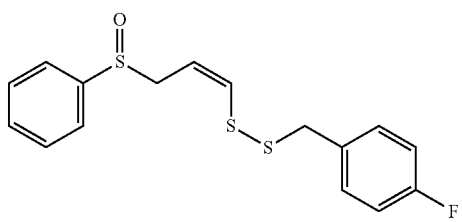 [SMILES: O=S(C/C=C\SSCc1ccc(F)cc1)c1ccccc1]

A target compound was obtained by the same manner as described in example 7 as a stereoisomer.
1:2 cis:trans (48.4%, separable)
Yield form: yellow oil
Rf=0.24 (n-hexane/ethyl acetate=2:1); (Z) 1H NMR (400 MHz, CD3OD) δ 7.57~7.65 (5H, m), 7.26~7.29 (2H, m), 7.00~7.05 (2H, m), 6.23 (1H, d, J=9.2 Hz), 5.40~5.47 (1H, m), 3.87 (2H, s), 3.79~3.84 (1H, m), 3.69~3.73 (1H, m).

<Example 9> Preparation of (E)-1-(4-methoxybenzyl)-2-(3-(phenylsulfinyl)prop-1-enyl)disulfane

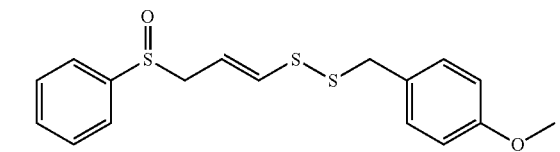 [SMILES: COc1ccc(CSS/C=C/CS(=O)c2ccccc2)cc1]

A target compound was obtained by the same manner as described in example 1 except that the compound of preparative example 5 was used instead of the compound of preparative example 1 in step 3 of example 1.
1:2 cis:trans (46.6%, separable)
Yield form: white solid
Rf=0.24 (n-hexane/ethyl acetate=2:1); (E) 1H NMR (400 MHz, CD3OD) δ 7.59~7.64 (5H, m), 7.17 (2H, d, J=8.8 Hz), 6.85 (2H, d, J=8.8 Hz), 6.09 (1H, d, J=14.8 Hz), 5.56~5.63 (1H, m), 3.79 (2H, s), 3.78 (3H, s), 3.72~3.76 (1H, m), 3.58~3.66 (1H, m).

<Example 10> Preparation of (Z)-1-(4-methoxybenzyl)-2-(3-(phenylsulfinyl)prop-1-enyl)disulfane

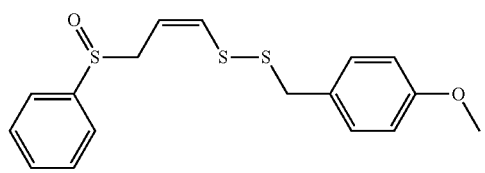 [SMILES: COc1ccc(CSS/C=C\CS(=O)c2ccccc2)cc1]

A target compound was obtained by the same manner as described in example 9 as a stereoisomer.
1:2 cis:trans (46.6%, separable)
Yield form: white solid
Rf=0.24 (n-hexane/ethyl acetate=2:1); (Z) 1H NMR (400 MHz, CDCl3) δ 7.59~7.62 (2H, m), 7.27~7.50 (3H, m), 7.17 (2H, d, J=8.8 Hz), 6.84 (2H, d, 8.8 Hz), 6.20 (1H, d, J=9.6 Hz), 5.43~5.49 (1H, m), 3.82 (2H, s), 3.80 (3H, s), 3.69~3.74 (1H, m), 3.60~3.66 (1H, m); 13C NMR (100 MHz, CDCl3) δ 143.2, 138.8, 131.5, 130.8, 129.4, 128.8, 124.6, 118.3, 114.3, 56.4, 55.6, 43.2.

<Example 11> Preparation of (E)-1-(4-chlorobenzyl)-2-(3-(phenylsulfinyl)prop-1-enyl)disulfane

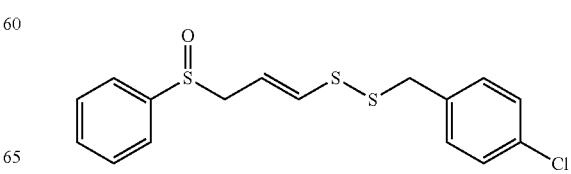

A target compound was obtained by the same manner as described in example 1 except that the compound of preparative example 6 was used instead of the compound of preparative example 1 in step 3 of example 1.

2:1 cis:trans (35%, separable)
Yield form: yellow oil
Rf=0.25 (n-hexane/ethyl acetate=2:1); (E) 1H NMR (400 MHz, CDCl3) δ 7.45~7.57 (5H, m), 7.24~7.26 (2H, m), 7.16 (2H, d, J=8.4 Hz), 5.94 (1H, d, J=14.8 Hz), 5.53~5.61 (1H, m), 3.79 (2H, s), 3.53~3.58 (1H, m), 3.41~3.46 (1H, m).

<Example 12> Preparation of (Z)-1-(4-chlorobenzyl)-2-(3-(phenylsulfinyl)prop-1-enyl)disulfane

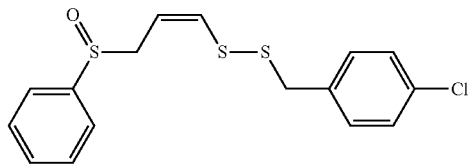 [SMILES: O=S(C/C=C\SSCc1ccc(Cl)cc1)c1ccccc1]

A target compound was obtained by the same manner as described in example 11 as a stereoisomer.

2:1 cis:trans (35%, separable)
Yield form: colorless oil
Rf=0.33 (n-hexane/ethyl acetate=2:1); (Z) 1H NMR (400 MHz, CDCl3) δ 7.49~7.58 (5H, m), 7.16 (2H, d, J=8.2 Hz), 7.17 (2H, d, J=8.2 Hz), 7.17 (2H, d, J=8.3 Hz), 6.16 (1H, d, J=9.4 Hz), 5.39~5.45 (1H, m), 3.79 (2H, s), 3.66~3.72 (1H, m). 3.57~3.64 (1H, m).

<Example 13> Preparation of (E)-1-(3,4-dichlorobenzyl)-2-(3-(phenylsulfinyl)prop-1-enyl)disulfane

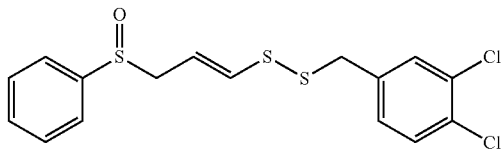 [SMILES: O=S(C/C=C/SSCc1ccc(Cl)c(Cl)c1)c1ccccc1]

A target compound was obtained by the same manner as described in example 1 except that the compound of preparative example 7 was used instead of the compound of preparative example 1 in step 3 of example 1.

1:2 cis:trans (37%, separable)
Yield form: colorless oil
Rf=0.23 (n-hexane/ethyl acetate=2:1); (E) 1H NMR (400 MHz, CDCl3) δ 7.52~7.57 (5H, m), 7.38 (1H, dd, J=8.2, 1.4 Hz), 7.33 (1H, s), 7.09 (1H, d, J=8.3 Hz), 5.98 (1H, d, J=14.8 Hz), 5.56~5.64 (1H, m), 3.76 (2H, s), 0.58~3.61 (1H, m), 3.42~3.49 (1H, m).

<Example 14> Preparation of (Z)-1-(3,4-dichlorobenzyl)-2-(3-(phenylsulfinyl)prop-1-enyl)disulfane

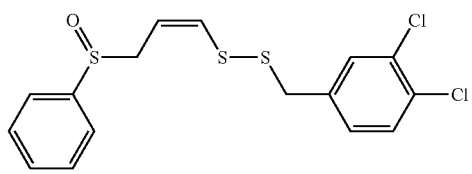 [SMILES: O=S(C/C=C\SSCc1ccc(Cl)c(Cl)c1)c1ccccc1]

A target compound was obtained by the same manner as described in example 13 as a stereoisomer.

1:2 cis:trans (37%, separable)
Yield form: colorless oil
Rf=0.31 (n-hexane/ethyl acetate=2:1); (Z) 1H NMR (400 MHz, CDCl3) δ 7.60~7.51 (5H, m), 7.38 (1H, d, J=8.2 Hz), 7.34 (1H, d, J=1.8 Hz), 7.10 (1H, dd, J=8.2, 1.9 Hz), 6.20 (1H, d, J=9.4 Hz), 5.43~5.50 (1H, m), 3.77 (2H, s), 3.69~3.75 (1H, m), 3.62~3.57 (1H, m).

<Example 15> Preparation of (E)-1-allyl-2-(3-(3-methoxyphenylsulfinyl)prop-1-enyl)disulfane

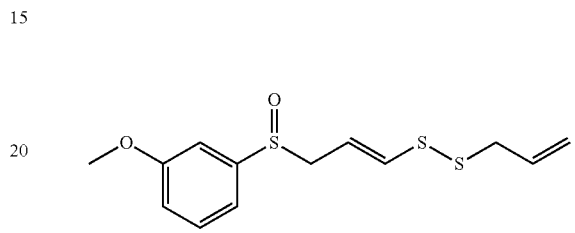

A target compound was obtained by the same manner as described in example 1 except that 3-methoxybenzenethiol or the corresponding isothiouronium salt (3-methoxyphenyl-SC(¼NH₂)NH₂ þ Br) was used instead of benzenethiol or the corresponding isothiouronium salt (Ph-SC(¼NH₂)NH₂ þ Br) in step 1 of example 1.

Rf=0.27 (n-hexane/ethyl acetate=2:1); (E) 1H NMR (400 MHz, CDCl3) δ 7.43 (1H, t, J=7.9 Hz), 7.17~7.18 (1H, m), 7.07 (1H, d, J=7.5 Hz), 7.01~7.04 (1H, m), 6.14 (1H, d, J=14.8 Hz), 5.64~5.84 (2H, m), 5.13~5.18 (2H, m), 3.86 (3H, s), 3.65 (1H, ddd, J=12.9, 7.9, 0.9 Hz), 3.53 (1H, ddd, J=12.9, 7.9, 0.9 Hz), 3.27 (2H, d, J=7.4 Hz); 13C NMR (100 MHz, CDCl3) δ 160.5, 144.3, 134.6, 132.6, 130.2, 119.4, 117.8, 116.4, 116.3, 108.9, 59.5, 55.8, 41.1.

<Example 16> Preparation of (Z)-1-allyl-2-(3-(3-methoxyphenylsulfinyl)prop-1-enyl)disulfane

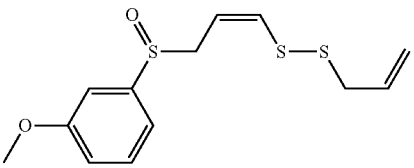 [SMILES: C=CCSS/C=C\CS(=O)c1cccc(OC)c1]

A target compound was obtained by the same manner as described in example 15 as a stereoisomer.

Rf=0.35 (n-hexane/ethyl acetate=2:1); 1H NMR (400 MHz, CDCl3) (Z) δ 7.40 (1H, t, J=7.9 Hz), 7.21~7.20 (1H, m), 7.13~7.10 (1H, m), 7.02 (1H, dd, J=8.2, 2.1 Hz), 6.48 (1H, d, J=9.4 Hz) 5.78~5.83 (1H, m), 5.54~5.61 (1H, m), 5.13~5.16 (1H, m), 3.87 (3H, s), 3.72~3.83 (1H, m), 3.60~3.70 (1H, m), 3.29 (2H, d, J=7.4 Hz); 13C NMR (100 MHz, CDCl3) δ 160.5, 144.3, 138.8, 133.2, 132.7, 130.2, 129.8, 128.2, 119.3, 118.4, 117.9, 116.6, 108.8, 56.2, 55.7, 42.1.

<Example 17> Preparation of (E)-1-(3-(3-methoxyphenylsulfinyl)prop-1-enyl)-2-propyldisulfane

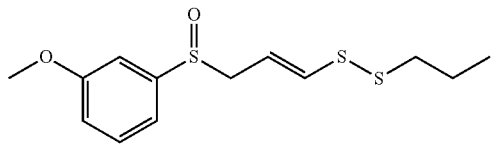 [SMILES: CCCSS/C=C/CS(=O)c1cccc(OC)c1]

A target compound was obtained by the same manner as described in example 15 except that the compound of preparative example 2 was used instead of the compound of preparative example 1 in step 3 of example 15.

Rf=0.27 (n-hexane/ethyl acetate=2:1); (E) 1H NMR (400 MHz, CDCl3) δ 7.41 (1H, t, J=8 Hz), 7.17~7.62 (1H, m), 7.07 (1H, dd, J=7.6, 1.2 Hz), 7.02 (1H, dd, J=7.6, 2.4 Hz), 6.15 (1H, d, J=14.8 Hz), 5.72~5.75 (1H, m), 3.87 (3H, s), 3.62~3.67 (1H, m), 3.51~3.65 (1H, m), 2.62 (2H, t, J=7.2 Hz), 1.63~1.71 (2H, m), 0.98 (3H, t, J=7.2 Hz).

<Example 18> Preparation of (Z)-1-(3-(3-methoxyphenylsulfinyl)prop-1-enyl)-2-propyldisulfane

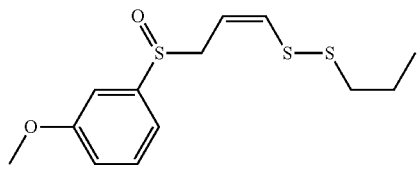 [SMILES: CCCSS/C=C\CS(=O)c1cccc(OC)c1]

A target compound was obtained by the same manner as described in example 17 as a stereoisomer.

Rf=0.35 (n-hexane/ethyl acetate=2:1); (Z) 1H NMR (400 MHz, CDCl3) δ7.40 (1H, t, J=8 Hz), 7.17~7.62 (1H, m), 7.13~7.11 (1H, m), 7.03~7.02 (1H, m), 6.50 (1H, d, J=9.6 Hz), 5.53~5.59 (1H, m), 3.87 (3H, s), 3.79~3.74 (1H, m), 3.69~3.64 (1H, m), 2.64 (2H, t, J=7.2 Hz), 1.63~1.69 (2H, m), 0.98 (3H, t, J=7.2 Hz).

<Example 19> Preparation of (E)-1-benzyl-2-(3-(3-methoxyphenylsulfinyl)prop-1-enyl)disulfane

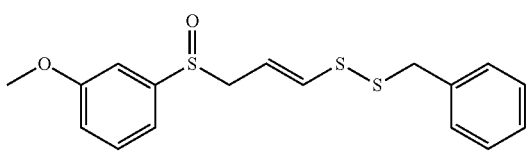 [SMILES: COc1cccc(S(=O)C/C=C/SSCc2ccccc2)c1]

A target compound was obtained by the same manner as described in example 15 except that the compound of preparative example 3 was used instead of the compound of preparative example 1 in step 3 of example 15.

Rf=0.23 (n-hexane/ethyl acetate=2:1); (E) 1H NMR (400 MHz, CDCl3) δ 7.40 (1H, t, J=8 Hz), 7.23~7.32 (5H, m), 7.16 (1H, m), 7.06 (1H, d, J=8 Hz), 7.02 (1H, dd, J=8.2, 2.5 Hz), 5.98 (1H, d, J=14.8 Hz), 5.55~5.64 (1H, m), 3.83 (3H, s), 3.59~3.54 (2H, m), 3.49~3.43 (2H, m); 13C NMR (100 MHz, CDCl3) δ 160.4, 144.2, 136.6, 134.2, 130.1, 129.5, 128.7, 127.7, 117.8, 116.4, 116.2, 108.9, 59.5, 55.7, 42.5.

<Example 20> Preparation of (Z)-1-benzyl-2-(3-(3-methoxyphenylsulfinyl)prop-1-enyl)disulfane

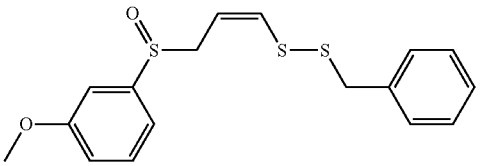 [SMILES: COc1cccc(S(=O)C/C=C\SSCc2ccccc2)c1]

A target compound was obtained by the same manner as described in example 19 as a stereoisomer.
1:1.5 cis:trans (40%, separable)
Yield form: yellow oil
Rf=0.31 (n-hexane/ethyl acetate=2:1); (Z) 1H NMR (400 MHz, CDCl3) δ 7.39 (1H, t, J=8 Hz), 7.24~7.32 (5H, m), 7.18 (1H, s), 7.08 (1H, d, J=8 Hz), 7.01 (1H, dd, J=8.2, 2.5 Hz), 6.17 (1H, d, J=9.4 Hz), 5.40~5.48 (1H, m), 3.85 (3H, s), 3.72~3.67 (1H, m), 3.63~3.57 (1H, m); 13C NMR (100 MHz, CDCl3) δ 160.5, 144.5, 138.3, 136.8, 130.2, 129.5, 128.7, 127.7, 118.3, 117.8, 116.5, 108.8, 56.2, 55.7, 43.5.

<Example 21> Preparation of (E)-1-(4-fluorobenzyl)-2-(3-(3-methoxyphenylsulfinyl)prop-1-enyl)disulfane

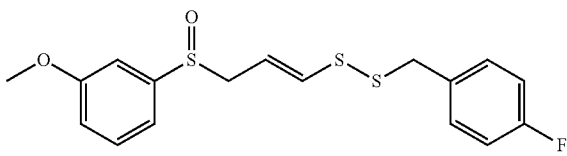 [SMILES: COc1cccc(S(=O)C/C=C/SSCc2ccc(F)cc2)c1]

A target compound was obtained by the same manner as described in example 15 except that the compound of preparative example 4 was used instead of the compound of preparative example 1 in step 3 of example 15.
1:2 cis:trans (38%, separable)
Yield form: yellow solid
Rf=0.23 (n-hexane/ethyl acetate=2:1); (E) 1H NMR (400 MHz, CDCl3) δ7.41 (1H, t, J=8 Hz), 7.24~7.20 (2H, m), 7.15~7.17 (1H, m), 7.07 (1H, dd, J=7.7, 1.1 Hz), 6.97~7.04 (3H, m), 5.99 (1H, d, J=14.8 Hz), 5.65~5.56 (1H, m), 3.84 (3H, s), 3.81 (2H, s), 3.61~3.56 (1H, m), 3.48~3.43 (1H, m).

<Example 22> Preparation of (Z)-1-(4-fluorobenzyl)-2-(3-(3-methoxyphenylsulfinyl)prop-1-enyl)disulfane

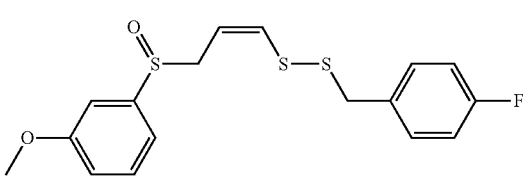

A target compound was obtained by the same manner as described in example 21 as a stereoisomer.

1:2 cis:trans (38%, separable)

Yield form: yellow solid

Rf=0.31 (n-hexane/ethyl acetate=2:1); (Z) 1H NMR (400 MHz, CDCl3) δ 7.40 (1H, t, J=7.9 Hz), 7.20~7.24 (2H, m), 7.18~7.19 (1H, m), 7.09 (1H, d, J=7.7 Hz), 6.95~7.05 (3H, m), 6.17 (1H, d, J=9.4 Hz), 5.42~5.49 (1H, m), 3.86 (1H, s), 3.83 (3H, s), 3.73~3.67 (1H, m), 3.59~3.63 (1H, m).

<Example 23> Preparation of (E)-1-(4-chlorobenzyl)-2-(3-(3-methoxyphenylsulfinyl)prop-1-enyl)disulfane

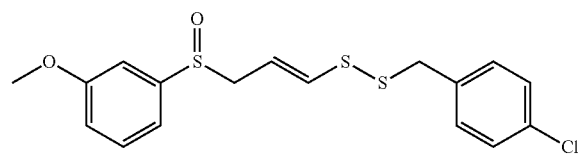 [SMILES: COc1cccc(S(=O)C/C=C/SSCc2ccc(Cl)cc2)c1]

A target compound was obtained by the same manner as described in example 15 except that the compound of preparative example 6 was used instead of the compound of preparative example 1 in step 3 of example 15.

2:1 cis:trans (38%, separable)

Yield form: colorless oil

Rf=0.23 (n-hexane/ethyl acetate=2:1); (E) 1H NMR (400 MHz, CDCl3) δ7.41 (1H, t, J=8 Hz, 7.29~7.25 (2H, m), 7.18~7.16 (3H, m), 7.07 (1H, d, J=7.6 Hz), 7.02 (1H, dd, J=8.2, 2.1 Hz), 5.98 (1H, d, J=14.8 Hz), 5.54~5.64 (1H, m), 3.85 (3H, s), 3.80 (2H, s), 3.57~3.52 (1H, m), 3.44~3.39 (1H, m); 13C NMR (100 MHz, CDCl3) δ 160.5, 144.1, 135.3, 133.9, 133.6, 130.8, 130.2, 128.8, 117.8, 116.5, 116.4, 108.9, 59.3, 55.7, 41.6.

<Example 24> Preparation of (Z)-1-(4-chlorobenzyl)-2-(3-(3-methoxyphenylsulfinyl)prop-1-enyl)disulfane

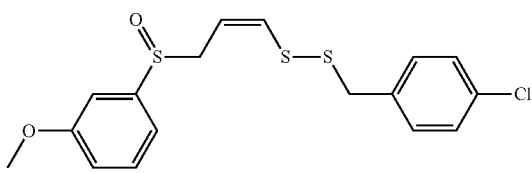 [SMILES: COc1cccc(S(=O)C/C=C\SSCc2ccc(Cl)cc2)c1]

A target compound was obtained by the same manner as described in example 23 as a stereoisomer.

2:1 cis:trans (38%, separable)

Yield form: colorless oil

Rf=0.31 (n-hexane/ethyl acetate=2:1); (Z) 1H NMR (400 MHz, CDCl3) δ 7.40 (1H, t, J=8.0 Hz), 7.29~7.25 (2H, m), 7.20~7.18 (3H, m), 7.08 (1H, d, J=7.7 Hz), 7.01 (1H, dd, J=8.2, 2.6 Hz), 6.18 (1H, d, J=9.4 Hz), 5.49~5.43 (1H, m), 3.85 (3H, s), 3.81 (2H, s), 3.73~3.69 (1H, m), 3.63~3.59 (1H, m); 13C NMR (100 MHz, CDCl3) δ 160.5, 144.3, 138.1, 135.4, 133.6, 133.0, 130.9, 130.8, 130.2, 130.2, 129.7, 128.8, 128.2, 118.6, 117.8, 116.5, 108.8, 56.1, 55.7, 42.6.

<Example 25> Preparation of (E)-1-(3,4-dichlorobenzyl)-2-(3-(3-methoxyphenylsulfinyl)prop-1-enyl)disulfane

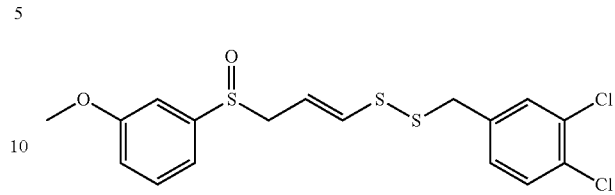

A target compound was obtained by the same manner as described in example 15 except that the compound of preparative example 7 was used instead of the compound of preparative example 1 in step 3 of example 15.

1:2 cis:trans (47%, separable)

Yield form: colorless oil

Rf=0.23 (n-hexane/ethyl acetate=2:1); (E) 1H NMR (400 MHz, CDCl3) δ 7.44~7.39 (2H, m), 7.38 (1H, d, J=8.2 Hz), 7.34 (1H, d, J=2 Hz), 7.16~7.15 (1H, m), 7.10~7.06 (2H, m), 7.02 (1H, dd, J=8.2, 2.5 Hz), 6.00 (1H, d, J=14.8 Hz), 5.65~5.57 (1H, m), 3.84 (3H, s), 3.76 (2H, s), 3.62~3.56 (1H, m), 3.47~3.42 (1H, m); 13C NMR (100 MHz, CDCl3) δ 160.5, 144.2, 137.1, 133.6, 132.6, 131.9, 131.3, 130.6, 130.2, 128.9, 117.7, 117.0, 116.4, 108.9, 76.8, 59.2, 55.8, 41.1.

<Example 26> Preparation of (Z)-1-(3,4-dichlorobenzyl)-2-(3-(3-methoxyphenylsulfinyl)prop-1-enyl)disulfane

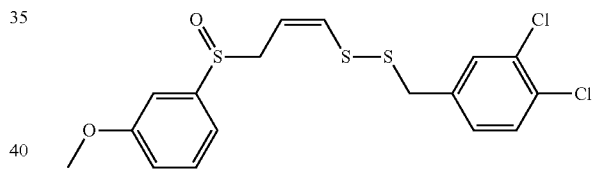

A target compound was obtained by the same manner as described in example 25 as a stereoisomer.

1:2 cis:trans (47%, separable)

Yield form: colorless oil

Rf=0.31 (n-hexane/ethyl acetate 2:1); (Z) 1H NMR (400 MHz, CDCl3) δ 7.42~7.37 (2H, m), 7.34 (1H, d, J=2.0 Hz), 7.19~7.17 (1H, m), 7.11~7.09 (2H, m), 7.01 (1H, dd, J=8.2, 2.5 Hz), 6.21 (1H, d, J=9.4 Hz), 5.48 (2H, m), 3.86 (3H, s), 3.76 (2H, s), 3.72~3.67 (1H, m), 3.60~3.54 (1H, m); 13C NMR (100 MHz, CDCl3) δ 160.5, 144.4, 137.9, 137.3, 132.6, 131.9, 131.4, 130.7, 130.3, 128.9, 119.0, 117.8, 116.5, 108.8, 56.1, 55.8, 42.1.

<Example 27> Preparation of (E)-1-allyl-2-(3-(4-methoxyphenylsulfinyl)prop-1-enyl)disulfane

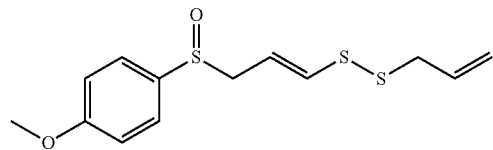 [SMILES: C=CCSS/C=C/CS(=O)c1ccc(OC)cc1]

A target compound was obtained by the same manner as described in example 1 except that 4-methoxybenzenethiol or the corresponding isothiouronium salt (4-methoxyphenyl-SC(¼NH$_2$)NH$_2$ þ Br) was used instead of benzenethiol or the corresponding isothiouronium salt (Ph-SC(¼NH$_2$)NH$_2$ þ Br) in step 1 of example 1.

2:1 cis:trans (16.3%, separable)

Yield form: colorless oil

Rf=0.20 (n-hexane/ethyl acetate=2:1); (E) IR (neat, cm-1) 2916, 2848, 2358, 1733, 1593, 1496, 1462, 1258, 1086, 1018, 893, 797; 1H NMR (400 MHz, CDCl3) δ 7.52 (2H, d J=8.8 Hz), 7.03 (2H, d J=8.8 Hz), 6.11 (1H, d, J=14.8 Hz), 5.63~5.82 (2H, m), 5.17 (2H, s), 5.14 (2H, d J=4.8 Hz), 3.86 (3H, s), 3.50~3.52 (2H, m), 3.27 (2H, d, J=7.6 Hz); 13C NMR (100 MHz, CDCl3) δ 134.6, 132.6, 130.9, 126.4, 119.4, 116.5, 114.8, 92.6, 59.6, 55.7, 41.1, 38.1.

<Example 28> Preparation of (Z)-1-allyl-2-(3-(4-methoxyphenylsulfinyl)prop-1-enyl)disulfane

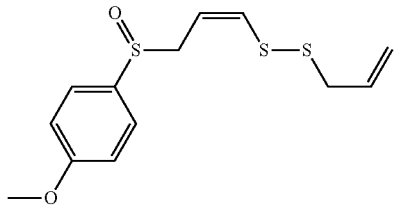 [SMILES: C=CCSS/C=C\CS(=O)c1ccc(OC)cc1]

A target compound was obtained by the same manner as described in example 27 as a stereoisomer.

2:1 cis:trans (16.3%, separable)

Yield form: colorless oil

Rf=0.20 (n-hexane/ethyl acetate=2:1); (Z) IR (neat, cm-1) 2916, 2848, 2358, 1592, 1494, 1455, 1303, 1251, 1172, 1129, 1085, 1046, 926, 830; 1H NMR (400 MHz, CDCl3) δ 7.55 (2H, d J=8.8 Hz), 7.02 (2H, d J=8.8 Hz), 6.45 (1H, d J=9.2 Hz), 5.72~5.83 (1H, m), 5.51~5.58 (1H, m), 5.12~5.17 (2H, m), 3.85 (3H, s), 3.62~3.72 (2H, m), 3.34 (2H, d, J=7.6 Hz); 13C NMR (100 MHz, CDCl3) δ 138.57, 133.88, 132.74, 126.38, 119.25, 118.59, 115.00, 114.83, 56.45, 55.67, 42.11, 34.79.

<Example 29> Preparation of (E)-1-(3-(4-methoxyphenylsulfinyl)prop-1-enyl)-2-propyldisulfane

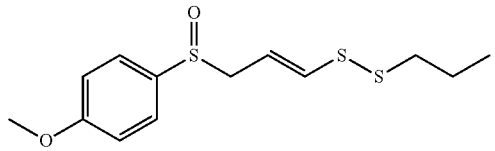 [SMILES: CCCSS/C=C/CS(=O)c1ccc(OC)cc1]

A target compound was obtained by the same manner as described in example 27 except that the compound of preparative example 2 was used instead of the compound of preparative example 1 in step 3 of example 27.

2:1 cis:trans (16.3%, separable)

Yield form: colorless oil

Rf=0.12 (n-hexane/ethyl acetate=2/1); (E) IR (neat, cm-1) 2961, 1715, 1592, 1494, 1302, 1251, 1086, 1027, 829; 1H NMR (400 MHz, CDCl3) δ 7.52 (2H, d, J=8.8 Hz), 7.03 (2H, d, J=8.8 Hz), 6.12 (1H, d, J=14.8 Hz), 5.63~5.71 (1H, m), 3.87 (3H, s), 3.58 (2H, dd, J=1.6, 6.8 Hz), 2.62 (2H, t, J=6.8 Hz), 1.65 (2H, q, J=7.2 Hz), 0.98 (3H, t, J=7.6 Hz); 13C NMR (100 MHz, CDCl3) δ 135.01, 133.29, 130.11, 118.92, 117.88, 116.47, 115.52, 108.83, 59.59, 55.74, 40.26, 35.34, 22.48, 13.17.

<Example 30> Preparation of (Z)-1-(3-(4-methoxyphenylsulfinyl)prop-1-enyl)-2-propyldisulfane

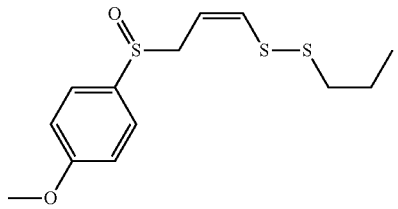 [SMILES: CCCSS/C=C\CS(=O)c1ccc(OC)cc1]

A target compound was obtained by the same manner as described in example 29 as a stereoisomer.

2:1 cis:trans (16.3%, separable)

Yield form: yellow oil

Rf=0.20 (n-hexane/ethyl acetate=2:1); (Z) IR (neat, cm-1) 2961, 1716, 1591, 1494, 1302, 1250, 1086, 1027, 829; 1H NMR (400 MHz, CDCl3) δ 7.55 (2H, d, J=8.8 Hz), 7.02 (2H, d, J=8.8 Hz), 6.48 (1H, d, J=9.6 Hz), 5.50~5.56 (1H, m), 3.86 (3H, s), 3.74~3.64 (2H, m), 2.63 (2H, t, J=6.8 Hz), 1.64 (2H, q, J=7.2 Hz), 0.97 (3H, t, J=7.6 Hz); 13C NMR (100 MHz, CDCl3) δ 160.48, 144.52, 139.42, 130.21, 117.89, 117.84, 116.55, 108.75, 56.29, 55.75, 41.25, 22.34, 13.11.

<Example 31> Preparation of (Z)-1-benzyl-2-(3-(4-methoxyphenylsulfinyl)prop-1-enyl)disulfane

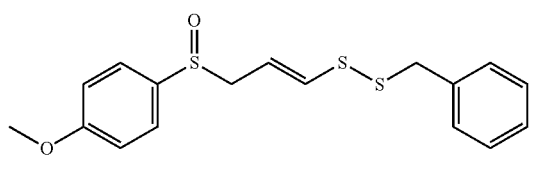 [SMILES: COc1ccc(S(=O)C/C=C/SSCc2ccccc2)cc1]

A target compound was obtained by the same manner as described in example 27 except that the compound of preparative example 3 was used instead of the compound of preparative example 1 in step 3 of example 27.

2:1 cis:trans (32.3%, separable)

Yield form: yellow oil

Rf=0.24 (n-hexane/ethyl acetate=2/1); (E) IR (neat, cm-1) 2919, 1590, 1490, 1455, 1288, 1247, 1171, 1087, 1028, 822; 1H NMR (400 MHz, CDCl3) δ 7.51 (2H, d, J=8.8 Hz), 7.03 (2H, d, J=8.8 Hz), 7.23~7.31 (5H, m), 5.96 (1H, d, J=14.8 Hz), 5.54~5.61 (1H, m), 4.83 (3H, s), 3.49~3.52 (2H, m); 13C NMR (100 MHz, CDCl3) δ 134.1, 133.3, 129.5, 128.7, 127.8, 126.4, 116.6, 114.8, 59.7, 55.7, 42.6, 38.1.

<Example 32> Preparation of (Z)-1-benzyl-2-(3-(4-methoxyphenylsulfinyl)prop-1-enyl)disulfane

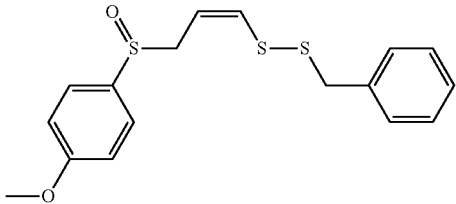 [SMILES: COc1ccc(S(=O)C/C=C\SSCc2ccccc2)cc1]

A target compound was obtained by the same manner as described in example 31 as a stereoisomer.

2:1 cis:trans (32.3%, separable)

Yield form: colorless oil

Rf=0.24 (n-hexane/ethyl acetate=2/1); (Z) IR (neat, cm-1) 2914, 1733, 1591, 1492, 1454, 1301, 1247, 1170, 1085, 1025, 826; 1H NMR (400 MHz, CDCl3) δ 7.53 (2H, d, J=8.8 Hz), 7.01 (2H, d, J=8.8 Hz), 7.24~7.33 (5H, m), 6.16 (1H, d, J=9.2 Hz), 5.39~5.45 (1H, m), 3.84 (3H, s), 3.59~3.68 (2H, m); 13C NMR (100 MHz, CDCl3) δ 138.2, 129.5, 129.1, 128.7, 127.7, 126.4, 118.4, 114.8, 114.6, 56.4, 55.6, 43.6.

<Example 33> Preparation of (E)-1-(4-fluorobenzyl)-2-(3-(4-methoxyphenylsulfinyl)prop-1-enyl) disulfane

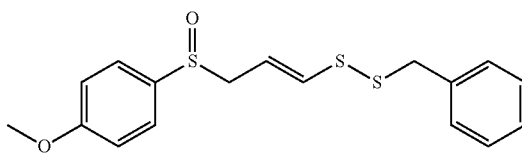

A target compound was obtained by the same manner as described in example 27 except that the compound of preparative example 4 was used instead of the compound of preparative example 1 in step 3 of example 27.

2:1 cis:trans (32.3%, separable)

Yield form: colorless oil

Rf=0.18 (n-hexane/ethyl acetate=2/1); (E) IR (neat, cm-1) 2962, 2837, 1593, 1508, 1495, 1457, 1408, 1303, 1252, 1222, 1156, 1086, 1027, 942, 830; 1H NMR (400 MHz, CDCl3) δ 7.51 (2H, d, J=8.8 Hz), 7.23 (2H, dd, J=5.6, 8.4 Hz), 6.97~7.04 (4H, m), 5.97 (1H, d, J=14.8 Hz), 5.57~5.65 (1H, m), 4.84 (3H, s), 3.81 (2H, s), 3.45~3.56 (2H, m); 13C NMR (100 MHz, CDCl3) δ 162.2, 133.9, 131.2, 131.1, 130.8, 126.4, 116.8, 116.1, 115.7, 115.5, 114.8, 59.6, 55.7, 41.6, 38.1.

<Example 34> Preparation of (Z)-1-(4-fluorobenzyl)-2-(3-(4-methoxyphenylsulfinyl)prop-1-enyl) disulfane

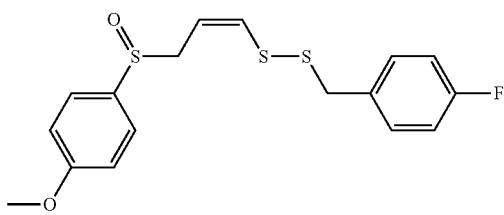 [SMILES: COc1ccc(S(=O)C/C=C\SSCc2ccc(F)cc2)cc1]

A target compound was obtained by the same manner as described in example 33 as a stereoisomer.

2:1 cis:trans (16.3%, separable)

Yield form: colorless oil

Rf=0.18 (n-hexane/ethyl acetate=2/1); (Z) IR (neat, cm-1) 2961, 2837, 1593, 1577, 1508, 1303, 1252, 1221, 1171, 1157, 1087, 1047, 829; 1H NMR (400 MHz, CDCl3) δ 7.53 (2H, d, J=8.8 Hz), 7.22 (2H, dd, J=5.6, 8.4 Hz), 6.97~7.02 (4H, m), 6.16 (1H, d, J=9.6 Hz), 5.39~5.46 (1H, m), 3.84 (3H, s), 3.82 (2H, s), 3.61~3.65 (2H, m); 13C NMR (100 MHz, CDCl3) δ 163.6, 138.1, 133.8, 131.2, 131.1, 126.4, 118.6, 115.7, 115, 5, 114.8, 56.4, 55.7, 42.6.

<Example 35> Preparation of (E)-1-(4-chlorobenzyl)-2-(3-(4-methoxyphenylsulfinyl)prop-1-enyl) disulfane

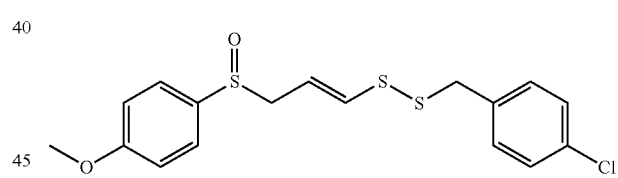

A target compound was obtained by the same manner as described in example 27 except that the compound of preparative example 6 was used instead of the compound of preparative example 1 in step 3 of example 27.

2:1 cis:trans (16.3%, separable)

Yield form: yellow oil

Rf=0.19 (n-hexane/ethyl acetate=2/1); (E) IR (neat, cm-1) 2963, 2837, 1593, 1494, 1461, 1440, 1406, 1319, 1256, 1179, 1147, 1087, 1026, 940, 831; 1H NMR (400 MHz, CDCl3) δ 7.51 (2H, d, J=8.8 Hz), 7.27 (2H, d, J=8.4 Hz), 7.18 (2H, d, J=8.4 Hz), 7.03 (2H, d, J=8.8 Hz), 5.93 (1H, d, J=14.8 Hz), 5.55~5.62 (1H, m), 3.84 (3H, s), 3.79 (2H, s), 3.44~3.56 (2H, m); 13C NMR (100 MHz, CDCl3) δ 162.2, 135.3, 133.8, 130.9, 128.9, 127.6, 126.4, 116.9, 114.8, 59.6, 55.7, 41.7, 37.9.

<Example 36> Preparation of (Z)-1-(4-chlorobenzyl)-2-(3-(4-methoxyphenylsulfinyl)prop-1-enyl)disulfane

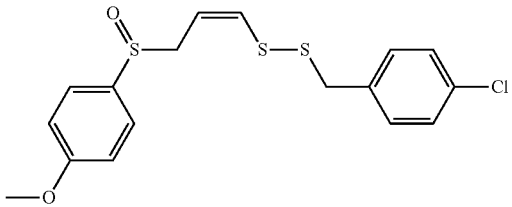 [SMILES: COc1ccc(S(=O)C/C=C\SSCc2ccc(Cl)cc2)cc1]

A target compound was obtained by the same manner as described in example 35 as a stereoisomer.

2:1 cis:trans (16.3%, separable)

Yield form: yellow oil

Rf=0.19 (n-hexane/ethyl acetate=2:1); (Z) IR (neat, cm-1) 2960, 2835, 1592, 1491, 1405, 1302, 1250, 1170, 1145, 1087, 1046, 829; 1H NMR (400 MHz, CDCl3) δ 7.52 (2H, d, J=8.8 Hz), 7.18~7.29 (4H, m), 7.01 (2H, d, J=8.8 Hz), 6.16 (1H, d, J=9.2 Hz), 5.39~5.46 (1H, m), 3.84 (3H, s), 3.81 (2H, s), 3.58~3.67 (2H, m); 13C NMR (100 MHz, CDCl3) δ 162.3, 137.9, 132.5, 130.9, 128.9, 126.4, 118.8, 114.8, 56.5, 56.4, 55.7, 46.1, 42.7.

<Example 37> Preparation of (E)-1-(3,4-dichlorobenzyl)-2-(3-(4-methoxyphenylsulfinyl)prop-1-enyl)disulfane

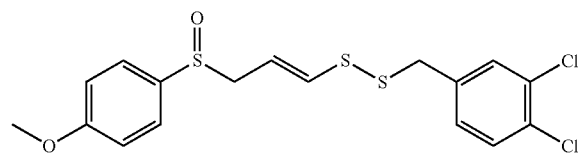 [SMILES: COc1ccc(S(=O)C/C=C/SSCc2ccc(Cl)c(Cl)c2)cc1]

A target compound was obtained by the same manner as described in example 27 except that the compound of preparative example 7 was used instead of the compound of preparative example 1 in step 3 of example 27.

2:1 cis:trans (16.3%, separable)

Yield form: yellow solid

Rf=0.20 (n-hexane/ethyl acetate=2/1); (E) IR (neat, cm-1) 2962, 1714, 1592, 1495, 1470, 1395, 1303, 1254, 1171, 1133, 1086, 1030, 827; 1H NMR (400 MHz, CDCl3) δ 7.51 (2H, d, J=8.8 Hz), 7.38 (2H, d, J=8 Hz), 7.34 (1H, d, J=2 Hz), 7.10 (1H, dd, J=2, 8 Hz), 7.03 (2H, d, J=8.8 Hz), 5.98 (1H, d, J=14.8 Hz), 5.58~5.62 (1H, m), 3.85 (3H, s), 3.76 (2H, s), 3.44~3.57 (2H, m); 13C NMR (100 MHz, CDCl3) δ 137.09, 133.59, 131.4, 130.6, 128.9, 126.3, 117.4, 114.9, 59.46, 55.68, 41.09.

<Example 38> Preparation of (Z)-1-(3,4-dichlorobenzyl)-2-(3-(4-methoxyphenylsulfinyl)prop-1-enyl)disulfane

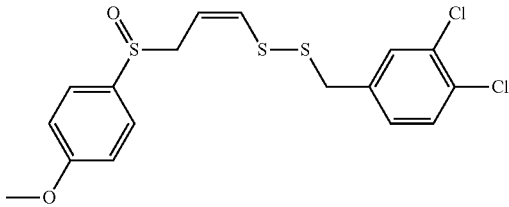 [SMILES: COc1ccc(S(=O)C/C=C\SSCc2ccc(Cl)c(Cl)c2)cc1]

A target compound was obtained by the same manner as described in example 37 as a stereoisomer.

2:1 cis:trans (16.3%, separable)

Yield form: yellow solid

Rf=0.20 (n-hexane/ethyl acetate=2/1); (Z) IR (neat, cm-1) 2963, 1592, 1494, 1469, 1440, 1408, 1303, 1260, 1171, 1087, 1029, 798; 1H NMR (400 MHz, CDCl3) δ 7.52 (2H, d, J=8.8 Hz), 7.38 (1H, d, J=8 Hz), 7.34 (1H, d, J=2 Hz), 7.10 (1H, dd, J=2, 8 Hz), 7.02 (2H, d, J=8.8 Hz), 6.57 (2H, d, J=9.2 Hz), 5.42~5.48 (1H, m), 3.85 (3H, s), 3.77 (2H, s), 3.57~3.69 (2H, m); 13C NMR (100 MHz, CDCl3) δ 162.2, 137.5, 137.1, 133.6, 132.4, 131.7, 131.2, 130.5, 128.7, 126.2, 118.9, 114.7, 56.1, 55.5, 41.9.

<Comparative Example 1> Preparation of E-Ajoene

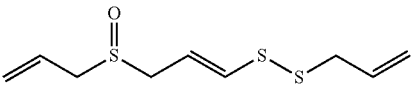

A target compound was obtained by the similar manner to the method used for the preparation of the compound of example above.

Colorless 2:1 Z:E mixture (48.5%, separable); Rr-0.36 (n-hexane/Ethyl acetate 1:2); (E)¹H NMR (400 MHz, CDCl₃) δ 6.39 (1H, d, J=14.8 Hz), 5.78~5.98 (3H, m), 5.39~5.49 (2H, m), 5.17~5.22 (2H, m), 3.48~3.65 (3H, m), 3.36~3.45 (3H, m); ¹³C NMR (100 MHz, CDCl₃) δ 134.7, 132.5, 125.5, 123.8, 119.2, 116.7, 54.3, 52.9, 41.3.

<Comparative Example 2> Preparation of Z-Ajoene

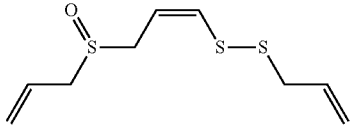

A target compound was obtained by the similar manner to the method used for the preparation of the compound of example above.

(Z)¹H NMR (400 MHz, CDCl₃) δ 6.53 (1H, d, J=9.2 Hz), 5.69~5.89 (3H, m), 5.37~5.45 (2H, m), 5.13~5.18 (2H, m), 3.46~3.65 (4H, m), 3.34~3.40 (2H, m). ¹³C NMR (100 MHz, CDCl₃) δ 138.9, 132.9, 125.9, 124.2, 119.6, 118.3, 55.2, 49.9, 42.4.

<Comparative Example 3> Preparation of (Z)-1-(3-(allylsulfinyl)prop-1-enyl)-2-benzyldisulfane

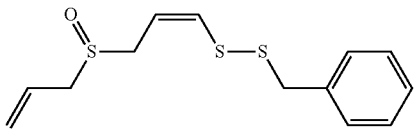 [SMILES: C=CCS(=O)C/C=C\SSCc1ccccc1]

A target compound was obtained by the similar manner to the method used for the preparation of the compound of example above. 2:1 cis:trans (34%, separable)

Rf=0.36 (n-hexane/ethyl acetate=1/2); $^1$H NMR (400 MHz, CD$_3$OD) (E) δ 7.16~7.26 (5H, m), 6.21 (1H, d, J=14.8 Hz), 5.71~5.85 (2H, m), 5.30~5.37 (2H, m), 3.86 (2H, s), 3.44~3.53 (2H, m), 3.29~3.39 (2H, m); $^{13}$C NMR (100 MHz, CD$_3$OD) δ (Z) (400 MHz, CD$_3$OD+CDCl$_3$) δ 7.16~7.22 (5H, m), 6.21 (1H, d, J=9.6 Hz), 5.77~5.88 (1H, m), 5.49~5.56 (1H, m), 5.32~5.39 (2H, m), 3.88 (2H, s), 3.46~3.58 (3H, m), 3.33~3.38 (1H, m); $^{13}$C NMR (100 MHz, CDCl$_3$) δ 139.4, 130.3, 129.2, 128.2, 126.9, 124.1, 118.7, 55.2, 50.1, 43.6.

<Comparative Example 4> Preparation of (Z)-1-allyl-2-(3-(benzylsulfinyl)prop-1-enyl)disulfane

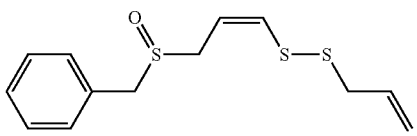 [SMILES: C=CCSS/C=C\CS(=O)Cc1ccccc1]

A target compound was obtained by the similar manner to the method used for the preparation of the compound of example above.

2:1 cis:trans (64.4%, separable)

Yield form: yellow oil

Rf=0.22 (n-hexane/ethyl acetate=2:1); (Z) 1H NMR (400 MHz, CDCl3) δ 7.31~7.42 (5H, m), 6.59 (1H, d, J=9.6 Hz), 5.76~5.87 (2H, m), 5.15~5.20 (2H, m), 3.98 (2H, s), 3.53~3.58 (2H, m), 3.43~3.49 (2H, m).

<Comparative Example 5> Preparation of (E)-1-allyl-2-(3-(benzylsulfinyl)prop-1-enyl)disulfane

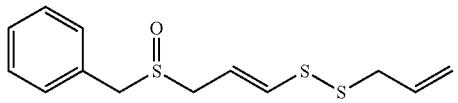 [SMILES: C=CCSS/C=C/CS(=O)Cc1ccccc1]

A target compound was obtained by the similar manner to the method used for the preparation of the compound of example above.

2:1 cis:trans (64.4%, separable)

Yield form: yellow oil R$_f$=0.22 (n-hexane/ethyl acetate=2: 1); (E)$^1$H NMR (400 MHz, CDCl$_3$) δ 7.26~7.41 (5H, m), 6.36 (1H, d, J=14.8 Hz), 5.79~5.99 (2H, m), 5.16~5.22 (2H, m), 3.98 (2H, s), 3.44~3.49 (2H, m), 3.29~3.37 (2H, m).

<Comparative Example 6> Preparation of (E)-1-(3-(benzylsulfinyl)prop-1-enyl)-2-propyldisulfane

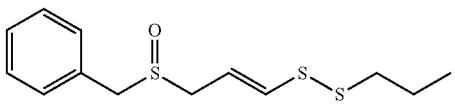 [SMILES: CCCSS/C=C/CS(=O)Cc1ccccc1]

A target compound was obtained by the similar manner to the method used for the preparation of the compound of example above.

1:1 cis:trans (60.7%, separable)

Yield form: yellow oil

Rf=0.21 (n-hexane/ethyl acetate=2:1); (E) 1H NMR (400 MHz, CDCl3) δ 7.27~7.42 (5H, m), 6.38 (1H, d, J=14.8 Hz), 5.92~5.99 (1H, m), 3.98 (2H, s), 3.45~3.50 (1H, m), 3.29~3.35 (1H, m), 2.72 (2H, t, J=7.2 Hz), 1.67~1.76 (2H, m), 1.01 (3H, t, J=7.2 Hz); 13C NMR (100 MHz, CDCl3) δ134.9, 130.1, 129.1, 128.5, 116.3, 56.9, 52.9, 40.4, 22.5, 13.1.

<Comparative Example 7> Preparation of (E)-1-benzyl-2-(3-(benzylsulfinyl)prop-1-enyl)disulfane

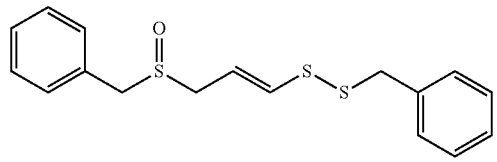 [SMILES: O=S(C/C=C/SSCc1ccccc1)Cc1ccccc1]

A target compound was obtained by the similar manner to the method used for the preparation of the compound of example above.

2:1 cis:trans (57.9%, separable)

Yield form: white solid

Rf=0.34 (n-hexane/ethyl acetate=2:1); (E) 1H NMR (400 MHz, CDCl3) δ 7.27~7.39 (10H, m), 6.14 (1H, d, J=14.8 Hz), 5.81~5.87 (1H, m), 3.93 (2H, s), 3.92 (2H, s), 3.33~3.38 (1H, m), 3.19~3.24 (1H, m).

<Comparative Example 8> Preparation of (E)-1-(3-(benzylsulfinyl)prop-1-enyl)-2-(4-fluorobenzyl)disulfane

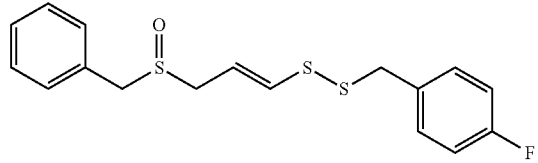 [SMILES: O=S(C/C=C/SSCc1ccc(F)cc1)Cc1ccccc1]

A target compound was obtained by the similar manner to the method used for the preparation of the compound of example above.

2:1 cis:trans (63.4%, separable)

Yield form: yellow solid

Rf=0.34 (n-hexane/ethyl acetate=1:1); (E) 1H NMR (400 MHz, CDCl3) δ 7.26~7.42 (7H, m), 6.98~7.26 (2H, m), 6.15 (1H, d, J=14.8 Hz), 5.81~5.89 (1H, m), 3.95 (2H, s), 3.90

(2H, s), 3.34~3.39 (1H, m), 3.19~3.25 (1H, m); 13C NMR (100 MHz, CDCl3) δ 133.9, 131.1, 130.9, 129.9, 129.0, 128.4, 117.1, 115.6, 115.4, 56.9, 52.7, 41.7.

<Comparative Example 9> Preparation of (Z)-1-(3-(benzylsulfinyl)prop-1-enyl)-2-(4-fluorobenzyl)disulfane

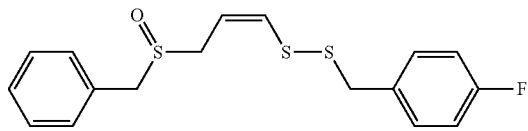 [SMILES: O=S(C/C=C\SSCc1ccc(F)cc1)Cc1ccccc1]

A target compound was obtained by the similar manner to the method used for the preparation of the compound of example above.

2:1 cis:trans (63.4%, separable)

Yield form: yellow solid

Rf=0.34 (n-hexane/ethyl acetate=1:1); (Z) 1H NMR (400 MHz, CDCl3) δ 7.23~7.39 (7H, m), 6.97~7.02 (2H, m), 6.26 (1H, d, J=9.2 Hz), 5.63~5.69 (1H, m), 3.95 (2H, s), 3.90 (2H, s), 3.37~3.51 (1H, m), 3.65~3.71 (1H, m); 13C NMR (100 MHz, CDCl3) δ 137.7, 130.7, 129.7, 128.7, 128.1, 117.9, 115.1, 57.2, 49.3, 42.3.

Formulas of the compounds prepared in examples 1 to 38 are shown in table 1 below.

TABLE 1

| Example | Formula |
|---|---|
| 1 | |
| 2 | |
| 3 | |
| 4 | |
| 5 | |
| 6 | |

TABLE 1-continued

| Example | Formula |
|---|---|
| 7 | phenyl-S(=O)-CH2-CH=CH-S-S-CH2-(4-fluorophenyl), E-isomer |
| 8 | phenyl-S(=O)-CH2-CH=CH-S-S-CH2-(4-fluorophenyl), Z-isomer |
| 9 | phenyl-S(=O)-CH2-CH=CH-S-S-CH2-(4-methoxyphenyl), E-isomer |
| 10 | phenyl-S(=O)-CH2-CH=CH-S-S-CH2-(4-methoxyphenyl), Z-isomer |
| 11 | phenyl-S(=O)-CH2-CH=CH-S-S-CH2-(4-chlorophenyl), E-isomer |
| 12 | phenyl-S(=O)-CH2-CH=CH-S-S-CH2-(4-chlorophenyl), Z-isomer |
| 13 | phenyl-S(=O)-CH2-CH=CH-S-S-CH2-(3,4-dichlorophenyl), E-isomer |
| 14 | phenyl-S(=O)-CH2-CH=CH-S-S-CH2-(3,4-dichlorophenyl), Z-isomer |
| 15 | (3-methoxyphenyl)-S(=O)-CH2-CH=CH-S-S-CH2-CH=CH2, E-isomer |

TABLE 1-continued

| Example | Formula |
|---|---|
| 16 | (Z)-1-methoxy-3-[(3-(propa-2-en-1-yldisulfanyl)prop-2-en-1-yl)sulfinyl]benzene |
| 17 | (E)-1-methoxy-3-[(3-(propyldisulfanyl)prop-2-en-1-yl)sulfinyl]benzene |
| 18 | (Z)-1-methoxy-3-[(3-(propyldisulfanyl)prop-2-en-1-yl)sulfinyl]benzene |
| 19 | (E)-1-[(3-(benzyldisulfanyl)prop-2-en-1-yl)sulfinyl]-3-methoxybenzene |
| 20 | (Z)-1-[(3-(benzyldisulfanyl)prop-2-en-1-yl)sulfinyl]-3-methoxybenzene |
| 21 | (E)-1-[(3-((4-fluorobenzyl)disulfanyl)prop-2-en-1-yl)sulfinyl]-3-methoxybenzene |
| 22 | (Z)-1-[(3-((4-fluorobenzyl)disulfanyl)prop-2-en-1-yl)sulfinyl]-3-methoxybenzene |
| 23 | (E)-1-[(3-((4-chlorobenzyl)disulfanyl)prop-2-en-1-yl)sulfinyl]-3-methoxybenzene |
| 24 | (Z)-1-[(3-((4-chlorobenzyl)disulfanyl)prop-2-en-1-yl)sulfinyl]-3-methoxybenzene |

(Note: the Formula column contains chemical structure drawings; textual names are approximations based on the drawn structures.)

TABLE 1-continued

| Example | Formula |
|---|---|
| 25 | 3-methoxyphenyl sulfinyl-CH₂-CH=CH-S-S-CH₂-(3,4-dichlorophenyl) (E) |
| 26 | 3-methoxyphenyl sulfinyl-CH₂-CH=CH-S-S-CH₂-(3,4-dichlorophenyl) (Z) |
| 27 | 4-methoxyphenyl sulfinyl-CH₂-CH=CH-S-S-CH₂-CH=CH₂ (E) |
| 28 | 4-methoxyphenyl sulfinyl-CH₂-CH=CH-S-S-CH₂-CH=CH₂ (Z) |
| 29 | 4-methoxyphenyl sulfinyl-CH₂-CH=CH-S-S-CH₂CH₂CH₃ (E) |
| 30 | 4-methoxyphenyl sulfinyl-CH₂-CH=CH-S-S-CH₂CH₂CH₃ (Z) |
| 31 | 4-methoxyphenyl sulfinyl-CH₂-CH=CH-S-S-CH₂-phenyl (E) |
| 32 | 4-methoxyphenyl sulfinyl-CH₂-CH=CH-S-S-CH₂-phenyl (Z) |

TABLE 1-continued

| Example | Formula |
|---|---|
| 33 | |
| 34 | |
| 35 | |
| 36 | |
| 37 | |
| 38 | |

<Experimental Example 1> Evaluation of Cancer Proliferation Inhibitory Activity <1-1> Evaluation of Cancer Proliferation Inhibitory Activity The following experiment was performed to evaluate the cancer proliferation inhibitory activity of the compound according to the present invention.

Particularly, the cancer proliferation inhibitory activity of the compounds of comparative examples (Ajoene and the compounds isosteric to Ajoene wherein R1 is allyl or benzyl) and the compounds of examples of the present invention (the compounds not isosteric to Ajoene wherein $R^1$ is phenyl) was investigated in human cancer cell lines (renal cancer cell line (ACHN), breast cancer cell line (MDA-MB-231), colorectal cancer cell line (HCT-15), prostate cancer cell line (PC-3), gastric cancer cell line (NUGC-3) and lung cancer cell line (NCl-H23)).

At this time, the cancer cell lines (renal cancer cell line (ACHN), breast cancer cell line (MDA-MB-231), colorectal cancer cell line (HCT-15), prostate cancer cell line (PC-3), gastric cancer cell line (NUGC-3) and lung cancer cell line (NCl-H23)) above were purchased from American Type Culture Collection (Manassas, Va., USA). Cells were cultured in RPMI 1640 supplemented with 10% fetal bovine serum, which were maintained 37° C. under 5% $CO_2$ wet atmosphere. The cells were distributed in a 96-well plate, which was not treated (treated only with 0.1% DMSO) or treated with the compounds of examples of the present (0.1 μM to 10 μM). 48 hours later, the cells were fixed in 50% trichloroacetic acid, followed by staining with 1% acetic acid containing 0.4% sulphorodamine B dissolved therein. The non-conjugated dye was removed by washing with 1% acetic acid, and the protein conjugated dye was extracted with 10 mM Tris base (pH 10.5). Then, $OD_{540}$ was measured with VersaMax microplate reader (Molecular devices, Sunnyvale, Calif., USA). $GI_{50}$ was calculated by using GraphPad Prism software (GraphPad Software, Inc., San Diego, Calif., USA). The results are shown in Table 2 below.

TABLE 2

| | | | | $GI_{50}(\mu M)$ | | | | | |
|---|---|---|---|---|---|---|---|---|---|
| | Isomer | $R^1$ | $R^2$ | ACHN | MDA-MB-231 | PC-3 | NUGC-3 | HCT-15 | NCI-H23 |
| Comparative Example 2 | Z | allyl | allyl | >10 | >10 | >10 | >10 | >10 | >10 |
| Comparative Example 3 | Z | allyl | benzyl | 3.26 | 4.64 | 2.31 | 2.05 | 4.96 | 3.59 |
| Comparative Example 4 | E | benzyl | allyl | 5.32 | | 3.28 | 8.07 | 5.93 | 5.98 |
| Comparative Example 5 | Z | benzyl | allyl | 4.43 | 5.45 | 6.85 | 10.30 | 9.10 | 4.41 |
| Comparative Example 6 | E | benzyl | propyl | | 2.19 | | 3.27 | 3.03 | 2.93 |
| Comparative Example 7 | E | benzyl | benzyl | 4.22 | | 3.88 | | | 6.41 |
| Comparative Example 8 | E | benzyl | 4-FB | 4.10 | | 2.04 | | 2.27 | 2.83 |
| Comparative Example 9 | Z | benzyl | 4-FB | 2.32 | 3.24 | | | | |
| Example 3 | E | phenyl | propyl | | 2.15 | | 2.93 | 2.64 | 2.80 |
| Example 5 | E | phenyl | benzyl | | | 3.19 | 3.71 | 3.97 | 2.98 |
| Example 9 | E | phenyl | 4-MB | 2.94 | 1.54 | 2.72 | 1.43 | 3.03 | 1.45 |
| Example 10 | Z | phenyl | 4-MB | 2.72 | 3.58 | 4.24 | 1.66 | 2.33 | 2.03 |

(4-FB: 4-fluorobenzyl; and
4-MB: 4-methoxybenzyl)

As shown in Tale 2, the cancer proliferation inhibitory activity of the compounds of examples 3, 5, 9 and 10, which were the compounds wherein $R^1$ is phenyl, was higher than that of the compounds of comparative examples 2~9, which were the compounds wherein $R^1$ is allyl or benzyl, and Ajoene.

<1-2> Evaluation of Cancer Proliferation Inhibitory Activity of Ajoene Non-Isosteric Compound Based on the results obtained in experimental example 1-1 above, the derivatives wherein $R^1$ is phenyl were additionally synthesized. The cancer proliferation inhibitory activity of the derivatives was evaluated by the same manner as described in experimental example 1-1. The results are shown in Table 3 below.

TABLE 3

| | | | | $GI_{50}(\mu M)$ | | | | | |
|---|---|---|---|---|---|---|---|---|---|
| | Isomer | $R^1$ | $R^2$ | ACHN | MDA-MB-231 | PC-3 | NUGC-3 | HCT-15 | NCI-H23 |
| Comparative Example 2 | Z | allyl | allyl | >10 | >10 | >10 | >10 | >10 | >10 |
| Example 3 | E | phenyl | propyl | 3.90 | 2.15 | 4.74 | 2.93 | 2.64 | 2.80 |
| Example 5 | E | phenyl | benzyl | 5.75 | 6.27 | 3.19 | 3.71 | 3.97 | 2.98 |
| Example 6 | Z | phenyl | benzyl | 5.42 | 3.96 | 5.35 | 3.25 | 6.48 | 4.91 |
| Example 7 | E | phenyl | 4-FB | 7.11 | 3.24 | 3.89 | 6.84 | 10.44 | 7.69 |
| Example 9 | E | phenyl | 4-MB | 2.94 | 1.54 | 2.720 | 1.43 | 3.03 | 1.45 |

TABLE 3-continued

| | Isomer | R$^1$ | R$^2$ | ACHN | MDA-MB-231 | PC-3 | NUGC-3 | HCT-15 | NCI-H23 |
|---|---|---|---|---|---|---|---|---|---|
| Example 10 | Z | phenyl | 4-MB | 2.72 | 3.58 | 4.24 | 1.66 | 2.33 | 2.03 |
| Example 11 | E | phenyl | 4-CB | 1.22 | 1.56 | 1.30 | 1.16 | 1.67 | 2.00 |
| Example 12 | Z | phenyl | 4-CB | 2.95 | 2.26 | 4.99 | 3.24 | 5.48 | 3.51 |
| Example 13 | Z | phenyl | 3,4-DCB | 1.97 | 7.50 | 2.30 | 1.77 | 2.78 | 2.92 |
| Example 14 | E | 3-MP | allyl | 7.68 | 4.78 | 4.55 | 8.51 | >10 | 7.35 |
| Example 15 | Z | 3-MP | allyl | 2.56 | 4.51 | 3.02 | 2.95 | 2.58 | 3.42 |
| Example 17 | E | 3-MP | propyl | 1.57 | 1.38 | 1.99 | 1.59 | 2.17 | 1.58 |
| Example 18 | Z | 3-MP | propyl | 2.06 | 2.43 | 1.92 | 1.71 | 1.34 | 1.59 |
| Example 19 | E | 3-MP | benzyl | 2.50 | 1.77 | 1.44 | 2.34 | 2.08 | 2.12 |
| Example 20 | Z | 3-MP | benzyl | 3.72 | 4.34 | 2.96 | 3.78 | 2.60 | 3.46 |
| Example 21 | E | 3-MP | 4-FB | 2.46 | 2.02 | 1.97 | 1.56 | 1.75 | 2.12 |
| Example 22 | Z | 3-MP | 4-FB | 3.85 | 4.41 | 3.04 | 3.67 | 3.01 | 2.71 |
| Example 23 | E | 3-MP | 4-CB | 5.47 | 3.12 | 3.76 | 5.92 | 4.37 | 4.85 |
| Example 24 | Z | 3-MP | 4-CB | 5.82 | 3.57 | 5.97 | 5.80 | 3.65 | 5.27 |
| Example 26 | Z | 3-MP | 3,4-DCB | >10 | >10 | 6.67 | 3.22 | 7.25 | >10 |
| Example 27 | E | 4-MP | allyl | 3.86 | 5.62 | 4.38 | 4.62 | 6.61 | 3.91 |
| Example 28 | Z | 4-MP | allyl | 5.06 | 7.28 | 4.47 | 3.77 | 3.94 | 4.24 |
| Example 29 | E | 4-MP | propyl | 1.65 | 2.20 | 2.41 | 2.04 | 1.48 | 1.41 |
| Example 30 | Z | 4-MP | propyl | 3.23 | 2.14 | 3.02 | 2.363 | 2.43 | 3.58 |
| Example 32 | Z | 4-MP | benzyl | 3.12 | 5.88 | 3.19 | 3.82 | 1.55 | 4.37 |
| Example 33 | E | 4-MP | 4-FB | 0.17 | 0.16 | 0.29 | 0.24 | 0.25 | 0.27 |
| Example 34 | Z | 4-MP | 4-FB | 1.34 | 1.09 | 1.35 | 2.65 | 1.45 | 1.49 |
| Example 35 | E | 4-MP | 4-CB | 0.88 | 1.16 | 1.05 | 1.08 | 0.88 | 0.97 |
| Example 36 | Z | 4-MP | 4-CB | 2.41 | 1.78 | 2.28 | 2.84 | 1.62 | 2.19 |
| Example 37 | E | 4-MP | 3,4-DCB | 3.75 | 4.19 | 5.17 | 5.48 | 3.32 | 3.09 |
| Example 38 | Z | 4-MP | 3,4-DCB | 5.19 | 2.07 | 4.36 | 4.61 | 7.18 | 3.33 |

(4-FB: 4-fluorobenzyl;

4-MB: 4-methoxybenzyl;

4-CB: 4-chlorobenzyl;

3,4-DCB: 3,4-dichlorobenzyl;

3-MP: 3-methoxyphenyl; and

4-MP: 4-methoxyphenyl)

As shown in Table 3, the cancer proliferation inhibitory activity of the derivatives wherein R$^1$ is phenyl, which were the compounds of examples of the present invention, was higher than that of the compounds of comparative examples 2~9 wherein R$^1$ is benzyl or allyl, and Ajoene. In particular, the derivatives wherein R$^1$ is substituted phenyl (examples 15~38) demonstrated more excellent cancer proliferation inhibitory activity than the compounds wherein R$^1$ s non-substituted phenyl.

Therefore, as confirmed in experimental examples 1-1 and 1-2, the novel organic sulfur compound of the present invention demonstrates excellent cancer proliferation inhibitory activity so that the novel compound of the invention can be effectively used as an active ingredient of a pharmaceutical composition for the prevention or treatment of cancer.

<Experimental Example 2> Evaluation of HDAC Inhibitory Activity

The following experiment was performed to evaluate the histone deacetylase (HDAC) inhibitory activity of the compound according to the present invention.

Particularly, HDAC enzyme analysis was performed based on a uniform fluorescence emission assay. First, the compounds of examples of the present invention or comparative example 1 were diluted at different concentrations, which were treated to the analysis buffer containing 25 mM HEPES (pH 8.0), 137 mM NaCl, 1 mM MgCl$_2$ and 2.7 mM KCL, followed by culture of the recombinant HDAC enzyme. 10 minutes later, Boc-Lys(acetyl)-AMC, the fluorescence inducing substrate, was added thereto, followed by further culture at 37° C. At this time, the concentration of the fluorescence inducing substrate and the culture time were adjusted according to the isotypes of the HDAC enzyme. The reaction was terminated by treating trypsin at room temperature for 20 minutes. The fluorescence intensity was measured using a fluorescence analyzer at an excitation wavelength of 380 nm and an emission wavelength of 460 nm, respectively. The inhibition rate was calculated from the measured fluorescence intensity of each well with comparing to that of the control well. IC$_{50}$ of the compound was calculated by analyzing the dose-reaction inhibition curve. The results are shown in Table 4.

The HDAC 8 inhibitory activity was presented as percentage of relative activity by the inhibitory activity of SAHA (Vorinostat) used as a reference compound. The results are shown in Table 4.

TABLE 4

| | Isomer | R¹ | R² | IC$_{50}$(μM) HDAC 1 | HDAC 6 | HDAC 8 | Inhibitory activity (%) HDAC 8 |
|---|---|---|---|---|---|---|---|
| Comparative Example 1 | E | allyl | allyl | | | | 73.4 |
| Comparative Example 2 | Z | allyl | allyl | | | | 52.5 |
| Example 1 | E | phenyl | allyl | | | | 32.1 |
| Example 2 | Z | phenyl | allyl | | | | 37.5 |
| Example 3 | E | phenyl | propyl | | | | 43.8 |
| Example 4 | Z | phenyl | propyl | | | | 115.2 |
| Example 5 | E | phenyl | benzyl | | | | 88.6 |
| Example 6 | Z | phenyl | benzyl | 3.89 | 49.15 | 0.043 | 129.1 |
| Example 7 | E | phenyl | 4-FB | | | | 37.1 |
| Example 8 | Z | phenyl | 4-FB | | | | 24.9 |
| Example 9 | E | phenyl | 4-MB | | | | 48.7 |
| Example 10 | Z | phenyl | 4-MB | | | | 73.8 |
| Example 11 | E | phenyl | 4-CB | | | | 74.4 |
| Example 12 | Z | phenyl | 4-CB | | | | 105.4 |
| Example 13 | E | phenyl | 3,4-DCB | | | | 76.6 |
| Example 14 | Z | phenyl | 3,4-DCB | | | | 146.4 |
| Example 15 | E | 3-MP | allyl | | | | 84.6 |
| Example 16 | Z | 3-MP | allyl | | | | 105.3 |
| Example 17 | E | 3-MP | propyl | | | | 78.4 |
| Example 18 | Z | 3-MP | propyl | 3.52 | 1.10 | 0.035 | 147.2 |
| Example 19 | E | 3-MP | benzyl | | | | 88.1 |
| Example 20 | Z | 3-MP | benzyl | | | | 114.3 |
| Example 21 | E | 3-MP | 4-FB | | | | 109.2 |
| Example 22 | Z | 3-MP | 4-FB | | | | 122.9 |
| Example 23 | E | 3-MP | 4-CB | | | | 72.6 |
| Example 24 | Z | 3-MP | 4-CB | 1.27 | | | 140.4 |
| Example 25 | E | 3-MP | 3,4-DCB | | | | 138.9 |
| Example 26 | Z | 3-MP | 3,4-DCB | | | | 161.9 |
| Example 27 | E | 4-MP | allyl | | | | 39.8 |
| Example 28 | Z | 4-MP | allyl | | | | 73.5 |
| Example 29 | E | 4-MP | propyl | | | | 69.9 |
| Example 30 | Z | 4-MP | propyl | | | 0.29 | 52.9 |
| Example 31 | E | 4-MP | benzyl | | | | 74.6 |
| Example 32 | Z | 4-MP | benzyl | 4.55 | 0.55 | 0.037 | 150.4 |
| Example 33 | E | 4-MP | 4-FB | | | | 111.7 |
| Example 34 | Z | 4-MP | 4-FB | | | | 68.1 |
| Example 35 | E | 4-MP | 4-CB | | | | 107.2 |
| Example 36 | Z | 4-MP | 4-CB | | | | 98.7 |
| Example 37 | E | 4-MP | 3,4-DCB | | | | 106.1 |
| Example 38 | Z | 4-MP | 3,4-DCB | | | | 55.5 |

(Inhibitory activity (%):(HDAC inhibitory activity of example compound/HDAC inhibitory activity of SAHA) × 100;
4-FB: 4-fluorobenzyl;
4-MB: 4-methoxybenzyl;
4-CB: 4-chlorobenzyl;
3,4-DCB: 3,4-dichlorobenzyl;
3-MP: 3-methoxyphenyl; and
4-MP: 4-methoxyphenyl)

As shown in Table 4, the compounds of examples of the present invention were confirmed to have higher inhibitory activity against HDAC 1, 6, and 8 than that of the compounds of comparative examples. In particular, the inhibitory activity against HDAC 8 was approximately 30~100 times higher than the inhibitory activity against HDAC1 and HDAC 6. IC$_{50}$ of the compound of example 18 against HDAC 8 was 35 nM.

Therefore, the compounds according to the present invention can inhibit HDAC 1, 6, and 8 enzymes in a concentration of nanomolar or micromolar units, and thus have inhibitory effect on HDAC related inflammatory diseases.

The compounds of examples of the present invention showed more excellent HDAC inhibitory activity than that of the compounds of comparative examples, and preferably they were able to inhibit HDAC 8 selectively, so that the compounds of the present invention have advantages of reducing side effects induced from the non-selective HDAC inhibitors and of increasing the inhibitory effect on cancer proliferation along with the therapeutic effect by inhibiting HDAC 8.

<Experimental Example 3> Evaluation of Anticancer Activity in Prostate Cancer Xenograft Model The following experiment was performed to evaluate the anticancer activity of the compounds according to the present invention in the prostate cancer xenograft model.

Particularly, 9×10⁶ PC-3 cells, human prostate cancer cells, were inoculated subcutaneously to the right side of female BALB/c nu/nu mice at 5 weeks of age (Nara Biotech, Seoul, Republic of Korea).

When the tumor size reached 40-60 mm³, the mice were randomly grouped (4 mice per group), which were the non-treated group (10% dimethylacetamide, 10% tween 80 and 80% distilled water), the groups treated with the compounds of comparative examples 1 and 2 (Ajoene, 50 mg/kg), the groups treated with the compounds of examples 18 and 32 (50 mg/kg), and the group treated with the positive control SAHA (Vorinostat, 100 mg/kg). The treatment was performed once a day for 16 days in total. During the treatment, the tumor size was measured with a vernier caliper, followed by evaluation according to the following formula: length (mm)×width (mm)×height (mm)/2. The weights were measured regularly.

Upon completion of the treatment (16 days later), the mice were sacrificed and the tumor weights were measured. All the experiments were performed according to the experiment protocol approved by Institutional Animal care and Use Committee (IACUC), Korea Research Institute of Bioscience and Biotechnology (KRIBB). The results are shown in FIGS. 1, 2, 3 and 4.

As shown in FIG. 1, it was confirmed that only normal weight increases were observed in the mice treated with SAHA (Vorinostat, 100 mg/kg), the compounds of comparative examples 1 and 2 (Ajoene, 50 mg/kg), and the compounds of examples 18 and 32 (50 mg/kg), suggesting that there was no visible toxicity.

Figure 2:
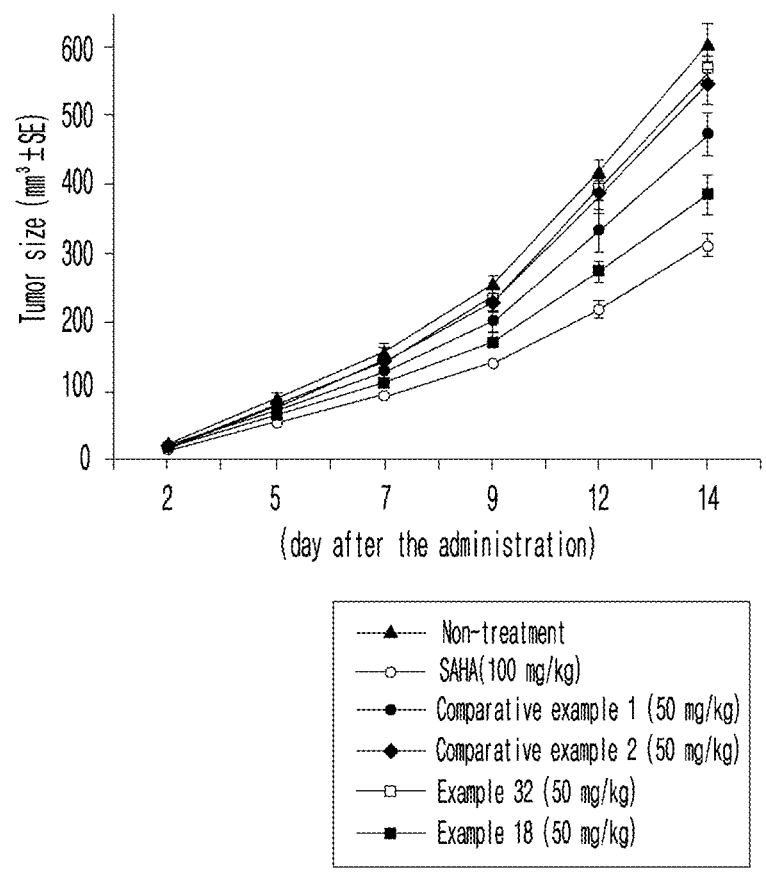
FIG. 2 is a graph illustrating the changes in tumor size (mm³±SE) according to the non-treatment and the administration of SAHA (Vorinostat, 100 mg/kg), the compounds of comparative examples 1 and 2 (Ajoene, 50 mg/kg) and the compounds of examples 18 and 32 (50 mg/kg) (measured from day 2 to day 14 after the administration).

As shown in FIG. 2, it was confirmed that the cancer proliferation was inhibited in the groups treated with SAHA (Vorinostat, 100 mg/kg), the compounds of comparative examples 1 and 2 (Ajoene, 50 mg/kg), and the compounds of examples 18 and 32 (50 mg/kg), compared with the non-treated group. In particular, the compound of example 18 was confirmed to inhibit cancer proliferation similarly to the positive control SAHA. Considering the dose of SAHA was twice that of the compound of example 18, the result above was quite encouraging.

Figure 3:
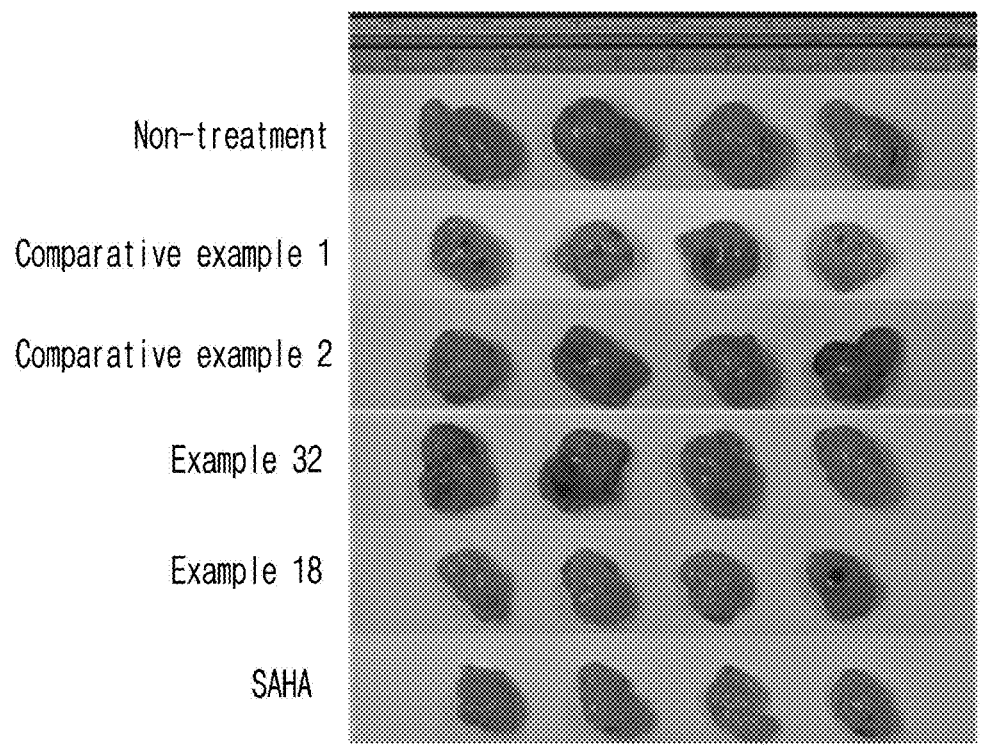
FIG. 3 is a set of photographs illustrating the cancer extracted from the mice non-treated or treated with SAHA (Vorinostat, 100 mg/kg), the compounds of comparative examples 1 and 2 (Ajoene, 50 mg/kg) and the compounds of examples 18 and 32 (50 mg/kg).

As shown in FIG. 3, it was confirmed that the tumor size was smaller in the groups treated with the compounds of examples of the present invention than in the non-treated group. The compounds of examples of the present invention were confirmed to inhibit cancer proliferation similarly to the positive control SAHA. Considering the dose of SAHA was twice that of the compounds of examples of the present invention, the result above was quite encouraging.

Figure 4:
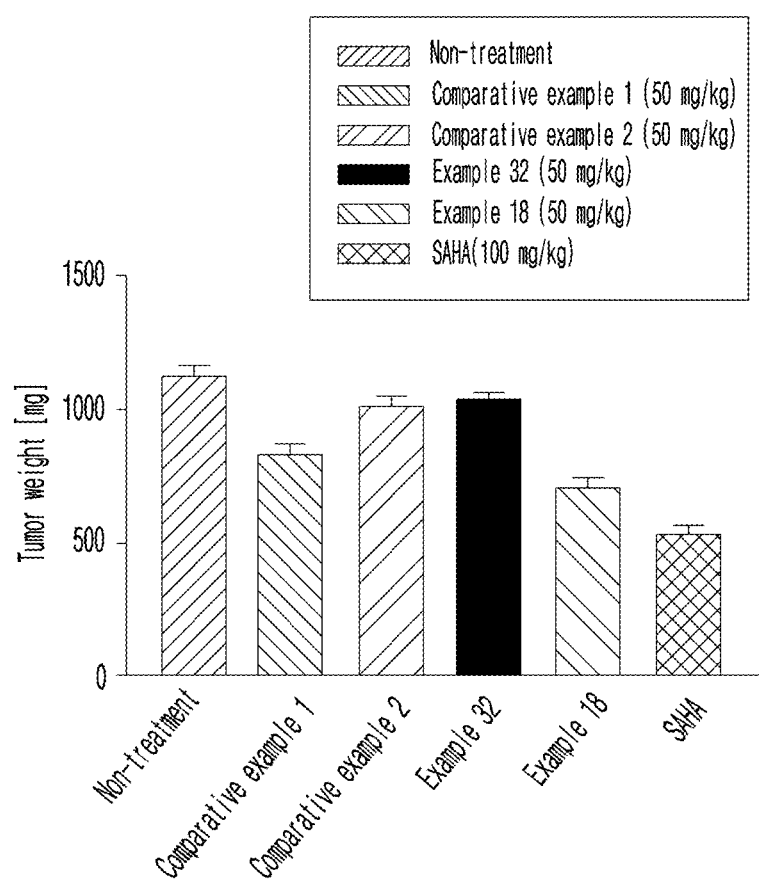
FIG. 4 is a graph illustrating the changes in the weight of tumor extracted from the mice non-treated or treated with SAHA (Vorinostat, 100 mg/kg), the compounds of comparative examples 1 and 2 (Ajoene, 50 mg/kg) and the compounds of examples 18 and 32 (50 mg/kg).

As shown in FIG. 4, the tumor weight in the group treated with the compound of example 18 of the present invention was lighter than the tumor weight in the non-treated group, the group treated with the compound of comparative example 1 and the group treated with the compound of comparative example 2 (Ajoene), and similar to that in the group treated with the positive control SAHA. Considering the dose of SAHA was twice that of the compound of example 18, the result above was quite encouraging.

Since the compounds according to the present invention, as confirmed in experimental example 3, have a visible effect on the inhibition of cancer proliferation, which is in particular similar or better effect than the positive control SAHA shows, the compounds of the present invention can be effectively used as an active ingredient of a pharmaceutical composition for the prevention or treatment of cancer or a health functional food composition for preventing or ameliorating cancer.

<Experimental Example 4> Evaluation of NO Generation Inhibitory Activity

To evaluate the anti-inflammatory activity of the compounds according to the present invention more intensively, the NO generation inhibitory activity was investigated.

Particularly, NO generation induced cells (cell density: 1.5×10$^5$/ml (400 ul/well), (+)S attachment for 24 hours) were cultured for 19 hours, which were non-treated or treated with LPS (1%, control group), the compounds of comparative examples 1 and 2, and the compounds of examples of the present invention at the concentrations of 2 uM and 10 uM respectively. Then, nitrite analysis was performed at 540 nm. The results are shown in FIG. 5 below.

Figure 5:
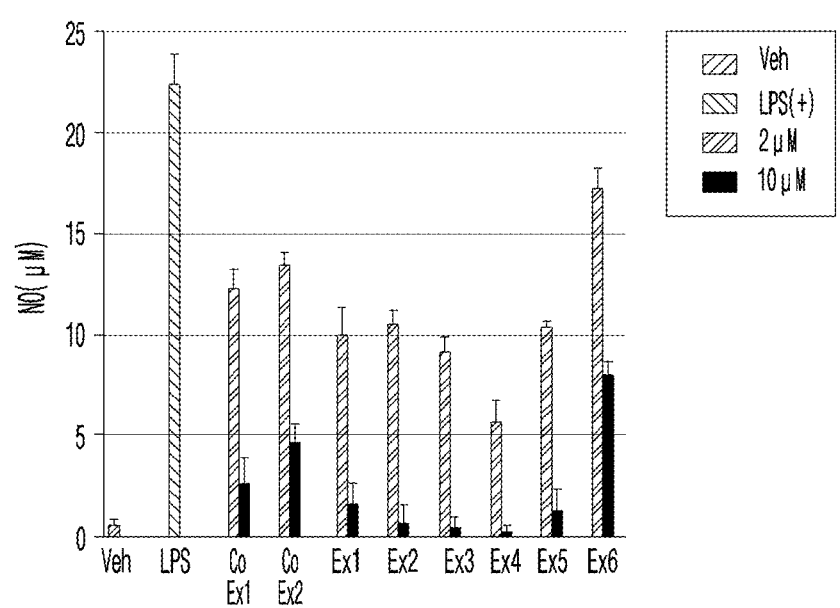
FIG. 5 is a graph illustrating the results of nitrite analysis at 540 nm after the non-treatment or treatment with LPS (1%), the compounds of comparative examples 1 and 2 and the compounds of examples 1~6 at the concentrations of 2 uM and 10 uM respectively.

As shown in FIG. 5, the compounds of examples 1~6 of the present invention demonstrated the NO generation inhibitory activity at the concentration of 2 uM, which was even more excellent than the NO generation inhibitory activity of the compound of comparative example (Ajoene). The NO generation inhibitory activity of the compounds of examples of the present invention was dose-dependent, so that the inhibitory activity was higher at the concentration of 10 uM than at the concentration of 2 uM. In particular, NO generation was hardly observed at the concentration of 10 uM.

Therefore, the compounds according to the present invention were confirmed to inhibit NO generation efficiently, so that they were evaluated to be effectively used as a pharmaceutical composition for the prevention or treatment of inflammatory diseases.

INDUSTRIAL APPLICABILITY

The novel organic sulfur compound according to the present invention is capable of excellently inhibiting histone deacetylated (HDAC) enzymes, particularly HDACs 1, 6 and 8 in a concentration of nanomolar or micromolar units and has been found to have an excellent effect against inflammatory diseases such as inflammatory bowel disease, and thus can be usefully used as a pharmaceutical composition for the prevention or treatment of inflammatory diseases, containing the same as an active ingredient.

In addition, particularly, the novel organic sulfur compound according to the present invention is capable of excellently inhibiting HDAC 8 in a concentration of nanomolar or micromolar units selectively, and has been found to be capable of inhibiting the proliferation of a renal cancer cell line (ACHN), a breast cancer cell line (MDA-MB-231), a colorectal cancer cell line (HCT-15), a prostate cancer cell line (PC-3), a gastric cancer cell line (NUGC-3) and a lung cancer cell line (NCl-H23), and thus can be usefully used for a pharmaceutical composition for the prevention or treatment of cancer, containing the same as an active ingredient.

What is claimed is:
1. A compound represented by formula 1 below, a stereoisomer thereof or a pharmaceutically acceptable salt thereof:

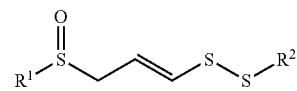

[Formula 1]

wherein,
$R^1$ is nonsubstituted or substituted phenyl,
wherein, the substituted phenyl can be substituted with one or more substitutents selected from the group consisting of hydroxy, amine, nitro, cyano, halogen, allyl, nonsubstituted or substituted $C_{1-5}$ straight or branched alkyl, and nonsubstituted or substituted $C_{1-5}$ straight or branched alkoxy,
wherein, the substituted alkyl and the substituted alkoxy can be independently substituted with one or more substitutents selected from the group consisting of hydroxy, halogen, amine, nitro and cyano;

R² is nonsubstituted or substituted $C_{2-6}$ straight or branched alkenyl, nonsubstituted or substituted $C_{1-5}$ straight or branched alkyl, nonsubstituted or substituted $C_{1-5}$ straight or branched alkoxy, or nonsubstituted or substituted $C_{1-3}$alkyl$C_{6-10}$aryl, wherein, the substituted alkenyl, the substituted alkyl, the substituted alkoxy and the substituted alkylaryl can be independently substituted with one or more substitutents selected from the group consisting of hydroxy, halogen, amine, nitro, cyano, nonsubstituted or substituted $C_{1-3}$ straight or branched alkyl and nonsubstituted or substituted $C_{1-3}$ straight or branched alkoxy.

2. The compound represented by formula 1, the stereoisomer thereof or the pharmaceutically acceptable salt thereof according to claim 1, wherein R¹ is nonsubstituted or substituted phenyl, wherein, the substituted phenyl can be substituted with one or more substitutents selected from the group consisting of hydroxy, halogen, nonsubstituted or substituted $C_{1-3}$ straight or branched alkyl, and nonsubstituted or substituted $C_{1-3}$ straight or branched alkoxy, wherein, the substituted alkyl and the substituted alkoxy can be independently substituted with one or more substitutents selected from the group consisting of hydroxy, halogen, amine, nitro and cyano.

3. The compound represented by formula 1, the stereoisomer thereof or the pharmaceutically acceptable salt thereof according to claim 1, wherein R² is allyl, nonsubstituted or substituted $C_{1-3}$ straight or branched alkyl, or nonsubstituted or substituted benzyl, wherein, the substituted alkyl and the substituted benzyl can be independently substituted with one or more substitutents selected from the group consisting of hydroxy, halogen, amine, nitro, cyano, nonsubstituted or substituted $C_{1-3}$ straight or branched alkyl and nonsubstituted or substituted $C_{1-3}$ straight or branched alkoxy.

4. The compound represented by formula 1, the stereoisomer thereof or the pharmaceutically acceptable salt thereof according to claim 1, wherein R¹ is

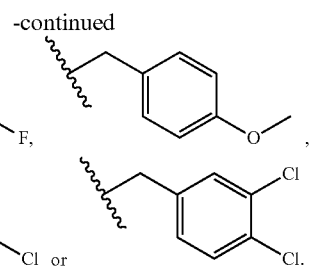

;

and
R² is

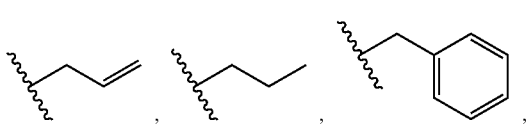

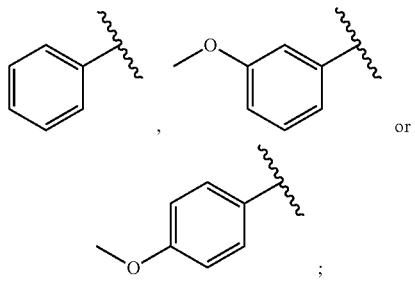

5. The compound represented by formula 1, the stereoisomer thereof or the pharmaceutically acceptable salt thereof according to claim 1, wherein the compound represented by formula 1 is selected from the following compounds:

(1) (E)-1-allyl-2-(3-(phenylsulfinyl)prop-1-enyl)disulfane;
(2) (Z)-1-allyl-2-(3-(phenylsulfinyl)prop-1-enyl)disulfane;
(3) (E)-1-(3-(phenylsulfinyl)prop-1-enyl)-2-propyldisulfane;
(4) (Z)-1-(3-(phenylsulfinyl)prop-1-enyl)-2-propyldisulfane;
(5) (E)-1-benzyl-2-(3-(phenylsulfinyl)prop-1-enyl)disulfane;
(6) (Z)-1-benzyl-2-(3-(phenylsulfinyl)prop-1-enyl)disulfane;
(7) (E)-1-(4-fluorobenzyl)-2-(3-(phenylsulfinyl)prop-1-enyl)disulfane;
(8) (Z)-1-(4-fluorobenzyl)-2-(3-(phenylsulfinyl)prop-1-enyl)disulfane;
(9) (E)-1-(4-methoxybenzyl)-2-(3-(phenylsulfinyl)prop-1-enyl)disulfane;
(10) (Z)-1-(4-methoxybenzyl)-2-(3-(phenylsulfinyl)prop-1-enyl)disulfane;
(11) (E)-1-(4-chlorobenzyl)-2-(3-(phenylsulfinyl)prop-1-enyl)disulfane;
(12) (Z)-1-(4-chlorobenzyl)-2-(3-(phenylsulfinyl)prop-1-enyl)disulfane;
(13) (E)-1-(3,4-dichlorobenzyl)-2-(3-(phenylsulfinyl)prop-1-enyl)disulfane;
(14) (Z)-1-(3,4-dichlorobenzyl)-2-(3-(phenylsulfinyl)prop-1-enyl)disulfane;
(15) (E)-1-allyl-2-(3-(3-methoxyphenylsulfinyl)prop-1-enyl)disulfane;
(16) (Z)-1-allyl-2-(3-(3-methoxyphenylsulfinyl)prop-1-enyl)disulfane;
(17) (E)-1-(3-(3-methoxyphenylsulfinyl)prop-1-enyl)-2-propyldisulfane;
(18) (Z)-1-(3-(3-methoxyphenylsulfinyl)prop-1-enyl)-2-propyldisulfane;
(19) (E)-1-benzyl-2-(3-(3-methoxyphenylsulfinyl)prop-1-enyl)disulfane;
(20) (Z)-1-benzyl-2-(3-(3-methoxyphenylsulfinyl)prop-1-enyl)disulfane;
(21) (E)-1-(4-fluorobenzyl)-2-(3-(3-methoxyphenylsulfinyl)prop-1-enyl)disulfane;
(22) (Z)-1-(4-fluorobenzyl)-2-(3-(3-methoxyphenylsulfinyl)prop-1-enyl)disulfane;
(23) (E)-1-(4-chlorobenzyl)-2-(3-(3-methoxyphenylsulfinyl)prop-1-enyl)disulfane;
(24) (Z)-1-(4-chlorobenzyl)-2-(3-(3-methoxyphenylsulfinyl)prop-1-enyl)disulfane;
(25) (E)-1-(3,4-dichlorobenzyl)-2-(3-(3-methoxyphenylsulfinyl)prop-1-enyl)disulfane;

(26) (Z)-1-(3,4-dichlorobenzyl)-2-(3-(3-methoxyphenylsulfinyl)prop-1-enyl)disulfane;
(27) (E)-1-allyl-2-(3-(4-methoxyphenylsulfinyl)prop-1-enyl)disulfane;
(28) (Z)-1-allyl-2-(3-(4-methoxyphenylsulfinyl)prop-1-enyl)disulfane;
(29) (E)-1-(3-(4-methoxyphenylsulfinyl)prop-1-enyl)-2-propyldisulfane;
(30) (Z)-1-(3-(4-methoxyphenylsulfinyl)prop-1-enyl)-2-propyldisulfane;
(31) (E)-1-benzyl-2-(3-(4-methoxyphenylsulfinyl)prop-1-enyl)disulfane;
(32) (Z)-1-benzyl-2-(3-(4-methoxyphenylsulfinyl)prop-1-enyl)disulfane;
(33) (E)-1-(4-fluorobenzyl)-2-(3-(4-methoxyphenylsulfinyl)prop-1-enyl)disulfane;
(34) (Z)-1-(4-fluorobenzyl)-2-(3-(4-methoxyphenylsulfinyl)prop-1-enyl)disulfane;
(35) (E)-1-(4-chlorobenzyl)-2-(3-(4-methoxyphenylsulfinyl)prop-1-enyl)disulfane;
(36) (Z)-1-(4-chlorobenzyl)-2-(3-(4-methoxyphenylsulfinyl)prop-1-enyl)disulfane;
(37) (E)-1-(3,4-dichlorobenzyl)-2-(3-(4-methoxyphenylsulfinyl)prop-1-enyl)disulfane; and
(38) (Z)-1-(3,4-dichlorobenzyl)-2-(3-(4-methoxyphenylsulfinyl)prop-1-enyl)disulfane.

6. A preparation method of the compound represented by formula 1 of claim 1 comprising the following steps, as shown in reaction formula 1 below:
preparing the compound represented by formula 3 from the compound represented by formula 2 (step 1);
preparing the compound represented by formula 4 from the compound represented by formula 3 prepared in step 1 above (step 2);
preparing the compound represented by formula 5 by reacting the compound represented by formula 4 prepared in step 2 above with p-TolSO$_2$SR$^2$ (para-toluenesulfonyl-SR$^2$) (step 3); and
preparing the compound represented by formula 1 from the compound represented by formula 5 prepared in step 3 above (step 4),

[Reaction Formula 1]

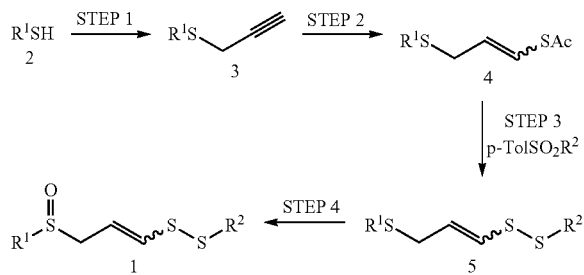

wherein,
R$^1$ and R$^2$ are as defined in the formula 1 of claim 1.

7. A pharmaceutical composition comprising the compound represented by formula 1 of claim 1, the stereoisomer thereof or the pharmaceutically acceptable salt thereof as an active ingredient for the prevention or treatment of cancer.

8. The pharmaceutical composition according to claim 7, wherein the compound is characterized by inhibiting HDAC (histone deacetylase) to prevent or treat cancer.

9. The pharmaceutical composition according to claim 7, wherein the cancer is at least one selected from the group consisting of pseudomyxoma, intrahepatic cholangiocarcinoma, liver cancer, thyroid cancer, colon cancer, testicular cancer, myelodysplastic syndrome, oral cancer, lip cancer, mycosis fungoides, acute myelogenous leukemia, acute lymphocytic leukemia, basal cell carcinoma, ovarian epithelial cancer, ovarian germ cell carcinoma, male breast cancer, brain cancer, pituitary adenoma, multiple myeloma, gallbladder cancer, biliary cancer, colon cancer, chronic myelogenous leukemia, chronic lymphocytic leukemia, choroidal melanoma, diffuse large B cell lymphoma, ampulla of Vater cancer, bladder cancer, peritoneal cancer, parathyroid cancer, adrenal gland cancer, sinunasal cancer, non-small cell lung cancer, non-Hodgkin's lymphoma, tongue cancer, small cell lung cancer, pediatric brain cancer, pediatric lymphoma, childhood leukemia, small bowel cancer, meningioma, esophagus cancer, renal cancer, kidney cancer, heart cancer, duodenal cancer, malignant soft tissue tumor, malignant bone cancer, malignant lymphoma, malignant mesothelioma, malignant melanoma, eye cancer, vulvar cancer, ureteral cancer, urethral cancer, cancer of unknown primary site, gastric lymphoma, gastric cancer, gastric carcinoid, gastrointestinal stromal cancer, Wilms' tumor, breast cancer, sarcoma, penile cancer, pharyngeal cancer, getstational trophoblatic disease, cervical cancer, endometrial cancer, uterine sarcoma, prostate cancer, metastatic bone cancer, metastatic brain cancer, mediastinal cancer, rectal cancer, rectal carcinoid, vaginal cancer, spinal cord cancer, pancreatic cancer, salivary gland cancer, Kaposi's sarcoma, Paget's disease, tonsil cancer, squamous cell carcinoma, adenocarcinoma of lung, lung cancer, squamous cell carcinoma of lung, skin cancer, anal cancer, rhabdomyosarcoma, laryngeal cancer, pleural cancer, and thymus cancer.

10. A health functional food composition comprising the compound represented by formula 1 of claim 1, the stereoisomer thereof or the pharmaceutically acceptable salt thereof as an active ingredient for preventing or ameliorating cancer.

11. A pharmaceutical composition comprising the compound represented by formula 1 of claim 1, the stereoisomer thereof or the pharmaceutically acceptable salt thereof as an active ingredient for the prevention or treatment of inflammatory diseases.

12. The pharmaceutical composition according to claim 11, wherein the compound is characterized by inhibiting HDAC (histone deacetylase) to prevent or treat inflammatory diseases.

13. The pharmaceutical composition for the prevention or treatment of inflammatory diseases according to claim 11, wherein the inflammatory disease is at least one selected from the group consisting of dermatitis, allergy, atopy, asthma, conjunctivitis, rhinitis, otitis, sore throat, tonsillitis, pneumonia, gastric ulcer, gastritis, Crohn's disease, inflammatory bowel disease, lupus, hepatitis, cystitis, nephritis, Sjogren's syndrome, multiple sclerosis, and acute and chronic inflammatory diseases.

14. A health functional food composition comprising the compound represented by formula 1 of claim 1, the stereoisomer thereof or the pharmaceutically acceptable salt thereof as an active ingredient for preventing or ameliorating inflammatory diseases.

15. A method treating cancer comprising the step of administering a therapeutically effective dose of the compound represented by formula 1 of claim 1, the stereoisomer thereof or the pharmaceutically acceptable salt thereof to a subject in need thereof.

16. A method treating inflammatory diseases comprising the step of administering a therapeutically effective dose of the compound represented by formula 1 of claim 1, the stereoisomer thereof or the pharmaceutically acceptable salt thereof to a subject in need thereof.

* * * * *